United States Patent [19]

Fujisawa et al.

[11] Patent Number: 5,241,053

[45] Date of Patent: Aug. 31, 1993

[54] FUSED PROTEINS COMPRISING GLYCOPROTEIN GD OF HSV-1 AND LTB

[75] Inventors: Yukio Fujisawa, Hyogo; Shuji Hinuma; Aki Mayumi, both of Osaka; Tatsuo Yamamoto, Chiba, all of Japan

[73] Assignee: Takeda Chemical Industries, Ltd., Osaka, Japan

[21] Appl. No.: 577,915

[22] Filed: Sep. 5, 1990

[51] Int. Cl.$^5$ .................. C07K 3/00; C07K 13/00; C07K 15/00; A61K 37/02

[52] U.S. Cl. .................. 424/89; 530/300; 530/350; 530/403; 530/405; 435/69.3; 435/69.7; 536/23.72; 424/92

[58] Field of Search .................. 514/12; 530/405, 403, 530/300, 350, 387; 435/92, 69.4, 172.3; 424/89, 92

[56] References Cited

U.S. PATENT DOCUMENTS

| | | | |
|---|---|---|---|
| 4,285,931 | 8/1981 | Limjuco et al. | 424/92 |
| 4,751,180 | 6/1988 | Cousens | 435/68 |
| 4,761,372 | 8/1988 | Maas et al. | 435/172.1 |
| 4,837,151 | 6/1989 | Stocker | 435/172.3 |
| 4,892,827 | 1/1990 | Pastan et al. | 435/193 |

FOREIGN PATENT DOCUMENTS

| | | |
|---|---|---|
| 0372928 | 6/1990 | European Pat. Off. |
| 8901041 | 3/1988 | PCT Int'l Appl. |
| WO88/02634 | 4/1988 | PCT Int'l Appl. |
| 8606635 | 11/1986 | World Int. Prop. O. |
| 8902924 | 4/1989 | World Int. Prop. O. |

OTHER PUBLICATIONS

Clements, Biological Abstracts, 90 (2), 1990, Ab. No. 15780 Schodel et al., Chemical Abstracts, 113, 1990 Ab. No. 38498h, p. 425.
Infection And Immunity, 57:1347–1350 (1989).
Abstracts of Annual Meeting of the American Society for Microbiology, p. 16, abstract No. S-6 (1988).
Journal of Bacteriology, 169, 5201–5208 (1987).
Yamamoto, et al., Molecular Organization of Heat-Labile Enterotoxin Genes Originating in *Escherichia coli* of Human Origin and Construction of Heat-Labile Toxoid-Producing Strains, Journal of Bacteriology, vol. 148, No. 3, pp. 983–987 (1981).
Yamamoto, et al., Release of Heat-Labile Enterotoxin Subunits by *Escherichia coli*, Journal of Bacteriology, vol. 150, No. 3, pp. 1482–1484 (1982).
Berman, et al., Protection for Genital Herpes Simplex Virus Type 2 Infection by Vaccination with Cloned Type 1 Glycoprotein D, Science, vol. 227, pp. 1409–1492 (1985).
Nozaki, et al., Expression of herpe simplex virus glycoprotein B gene in yeast, Virus Research, vol. 4, pp. 107–113 (1985).
Kino, et al., Immunogenicity of herpes simplex virus glycoprotein gB-1-related protein produced in yeast, Vaccine, vol. 7, pp. 155–160 (1989).

*Primary Examiner*—Lester L. Lee
*Assistant Examiner*—A. M. Davenport
*Attorney, Agent, or Firm*—David G. Conlin; Ronlad I. Eisenstein

[57] ABSTRACT

Disclosed are (1) a fused protein comprising heat-labile enterotoxin B subunit and a protein heterologous to heat-labile enterotoxin, (2) a recombinant DNA containing a nucleotide sequence coding for the above fused protein, (3) a transformant harboring the above recombinant DNA, (4) a method for producing the fused protein which comprises cultivating the above transformant, producing and accumulating the above fused protein in a culture, and collecting the fused protein, and (5) a method for purifying a fused protein comprising a herpes simplex virus surface antigen and heat-labile enterotoxin B subunit, which comprises cultivating a transformant harboring a recombinant DNA containing a nucleotide sequence coding for the fused protein, producing an accumulating the fused protein in a culture, collecting the fused protein and subjecting the collected fused protein to purification processes comprising cationic exchange chromatography and gel permeation chromatography.

3 Claims, 22 Drawing Sheets

FIG. 1

```
  1 Met Gly Gly Ala Ala Ala Arg Leu Gly Ala Val Ile Leu Phe Val Val
 17 Ile Val Gly Leu His Gly Val Arg Gly Lys Tyr Ala Leu Ala Asp Ala
 33 Ser Leu Lys Met Ala Asp Pro Asn Arg Phe Arg Gly Lys Asp Leu Pro
 49 Val Leu Asp Pro Leu Thr Asp Pro Pro Gly Val Arg Arg Val Tyr His
 65 Ile Gln Ala Gly Leu Pro Asp Pro Phe Gln Pro Pro Ser Leu Pro Ile
 81 Thr Val Tyr Tyr Ala Val Leu Glu Arg Ala Cys Arg Ser Val Leu Leu
 97 Asn Ala Pro Ser Glu Ala Pro Gln Ile Val Arg Gly Ala Ser Glu Asp
113 Val Arg Lys Gln Pro Tyr Asn Leu Thr Ile Ala Trp Phe Arg Met Gly
129 Gly Asn Cys Ala Ile Pro Ile Thr Val Met Glu Tyr Thr Glu Cys Ser
145 Tyr Asn Lys Ser Leu Gly Ala Cys Pro Ile Arg Thr Gln Pro Arg Trp
161 Asn Tyr Tyr Asp Ser Phe Ser Ala Val Ser Glu Asp Asn Leu Gly Phe
177 Leu Met His Ala Pro Ala Phe Glu Thr Ala Gly Thr Tyr Leu Arg Leu
193 Val Lys Ile Asn Asp Trp Thr Glu Ile Thr Gln Phe Ile Leu Glu His
209 Arg Ala Lys Gly Ser Cys Lys Tyr Ala Leu Pro Leu Arg Ile Pro Pro
225 Ser Ala Cys Leu Ser Pro Gln Ala Tyr Gln Gln Gly Val Thr Val Asp
241 Ser Ile Gly Met Leu Pro Arg Phe Ile Pro Glu Asn Gln Arg Thr Val
257 Ala Val Tyr Ser Leu Lys Ile Ala Gly Trp His Gly Pro Lys Ala Pro
273 Tyr Thr Ser Thr Leu Leu Pro Pro Glu Leu Ser Glu Thr Pro Asn Ala
289 Thr Gln Pro Glu Leu Ala Pro Glu Asp Pro Glu Asp Ser Ala Leu Leu
305 Glu Asp Pro Val Gly Thr Val Ala Pro Gln Ile Pro Pro Asn Trp His
321 Ile Pro Ser Ile Gln Asp Ala Ala Thr Pro Tyr His Pro Pro Ala Thr
337 Pro Asn Asn Met Gly Leu Ile Ala Gly Ala Val Gly Gly Ser Leu Leu
353 Ala Ala Leu Val Ile Cys Gly Ile Val Tyr Trp Met His Arg Arg Thr
369 Arg Lys Ala Pro Lys Arg Ile Arg Leu Pro His Ile Arg Glu Asp Asp
385 Gln Pro Ser Ser His Gln Pro Leu Phe Tyr
```

FIG. 2

```
   1  TTT AAA AAG CAG GGG TTA GGG AGT TGT TCG GTC ATA AGC TTC AGC
  46  GCG AAC GAC CAA CTA CCC CGA TCA TCA GTT ATC CTT AAG GTC TCT
  91  TTT GTG TGG TGC GTT CCG GTA TGG GGG GGG CTG CCG CCA GGT TGG
 136  GGG CCG TGA TTT TGT TTG TCG TCA TAG TGG GCC TCC ATG GGG TCC
 181  GCG GCA AAT ATG CCT TGG CGG ATG CCT CTC TCA AGA TGG CCG ACC
 226  CCA ATC GCT TTC GCG GCA AAG ACC TTC CGG TCC TGG ACC CGC TGA
 271  CCG ACC CTC CGG GGG TCC GGC GCG TGT ACC ACA TCC AGG CGG GCC
 316  TAC CGG ACC CGT TCC AGC CCC CCA GCC TCC CGA TCA CGG TTT ACT
 361  ACG CCG TGT TGG AGC GCG CCT GCC GCA GCG TGC TCC TAA ACG CAC
 406  CGT CGG AGG CCC CCC AGA TTG TCC GCG GGG CCT CCG AAG ACG TCC
 451  GGA AAC AAC CCT ACA ACC TGA CCA TCG CTT GGT TTC GGA TGG GAG
 496  GCA ACT GTG CTA TCC CCA TCA CGG TCA TGG AGT ACA CCG AAT GCT
 541  CCT ACA ACA AGT CTC TGG GGG CCT GTC CCA TCC GAA CGC AGC CCC
 586  GCT GGA ACT ACT ATG ACA GCT TCA GCG CCG TCA GCG AGG ATA ACC
 631  TGG GGT TCC TGA TGC ACG CCC CCG CGT TTG AGA CCG CCG GCA CGT
 676  ACC TGC GGC TCG TGA AGA TAA ACG ACT GGA CGG AGA TTA CAC AGT
 721  TTA TCC TGG AGC ACC GAG CCA AGG GCT CCT GTA AGT ACG CCC TCC
 766  CGC TGC GCA TCC CCC GTC AGC CTG CCT CTC CCC CAG GCC TAC C
 811  AGC AGG GGG TGA CGG TGG ACA GCA TCG GAT GCT GCC CCG CTT CA
 856  TCC CCG AGA ACC AGC GCA CCG TCG CCG TAT ACA GCT TGA AGA TCG
 901  CCG GGT GGC ACG GGC CCA AGG CCC CAT ACA CGA GCA CCC TGC TGC
 946  CCC CTG AGC TGT CCG AGA CCC CCA ACG CCA CGC AGC CAG AAC TCG
 991  CCC CGG AAG ACC CCG AGG ATT CGG CCC TCT TGG AGG ACC CCG TGG
1036  GGA CGG TGG CGC CGC AAA TCC CAC CAA ACT GGC ACA TCC CGT CGA
1081  TCC AGG ACG CCG CGA CGC CTT ACC ATC CCC CGG CCA CCC CGA ACA
1126  ACA TGG CCT GAT CGC CGC GCG GTG GCG GCA GTC TCC TGG CAG
1171  CCC TGG TCA TTT GCG GAA TTG TGT ACT GGA TGC ACC GCC GCA CTC
1216  GGA AAG CCC CAA AGC GCA TAC GCC TCC CCA CAT CCG GGA AGA CG
1261  ACC AGC CGT CCT CGC ACC AGC CCT TGT TTT ACT AGA TAC CCC CCC
1306  TTA ATG GGT GCG GGG GGT CAG GTC TGC GGG TTG GAT GGG ACC
1351  TTA ACT CCA TAC AAA GCG AGT CTG GAA GGG GGG AAA GGC GGA CAG
1396  TCG ATA AGT CGG TAG CGG GGG ACG CGC ACC TGT TCC GCC TGT CGC
1441  ACC CAC AGC TTT TTC GCG A
```

FIG. 3-1

```
                                                                Ala Pro
Ser Ser Pro Gly Thr Pro Gly Val Ala Ala Ala Thr Gln Ala Ala Asn
Gly Gly Pro Ala Thr Pro Ala Pro Pro Ala Pro Gly Pro Ala Pro Thr
Gly Asp Thr Lys Pro Lys Lys Asn Lys Lys Pro Lys Asn Pro Pro Pro
Pro Arg Pro Ala Gly Asp Asn Ala Thr Val Ala Ala Gly His Ala Thr
Leu Arg Glu His Leu Arg Asp Ile Lys Ala Lys Asn Thr Asp Ala Asn
Phe Tyr Val Cys Pro Pro Pro Thr Gly Ala Thr Val Val Gln Phe Glu
Gln Pro Arg Arg Cys Pro Thr Arg Pro Glu Gly Gln Asn Tyr Thr Glu
Gly Ile Ala Val Val Phe Lys Glu Asn Ile Ala Pro Tyr Lys Phe Lys
Ala Thr Met Tyr Tyr Lys Asp Val Thr Val Ser Gln Val Trp Phe Gly
His Arg Tyr Ser Gln Phe Met Gly Ile Phe Glu Asp Arg Ala Pro Val
Pro Phe Glu Glu Val Ile Asp Lys Ile Asn Ala Lys Gly Val Cys Arg
Ser Thr Ala Lys Tyr Val Arg Asn Asn Leu Glu Thr Thr Ala Phe His
Arg Asp Asp His Glu Thr Asp Met Glu Leu Lys Pro Ala Asn Ala Ala
Thr Arg Thr Ser Arg Gly Trp His Thr Thr Asp Leu Lys Tyr Asn Pro
Ser Arg Val Glu Ala Phe His Arg Tyr Gly Thr Thr Val Asn Cys Ile
Val Glu Glu Val Asp Ala Arg Ser Val Tyr Pro Tyr Asn Glu Phe Val
Leu Ala Thr Gly Asp Phe Val Tyr Met Ser Pro Phe Tyr Gly Tyr Arg
Glu Gly Ser His Thr Glu His Thr Ser Tyr Ala Ala Asp Arg Phe Lys
Gln Val Asp Gly Phe Tyr Ala Arg Asp Leu Thr Thr Lys Ala Arg Ala
Thr Ala Pro Thr Thr Arg Asn Leu Leu Thr Thr Pro Lys Phe Thr Val
Ala Trp Asp Trp Val Pro Lys Arg Pro Ser Val Cys Thr Met Thr Lys
Trp Gln Glu Val Asp Glu Met Leu Arg Ser Glu Tyr Gly Gly Ser Phe
Arg Phe Ser Ser Asp Ala Ile Ser Thr Thr Phe Thr Thr Asn Leu Thr
Glu Tyr Pro Leu Ser Arg Val Asp Leu Gly Asp Cys Ile Gly Lys Asp
Ala Arg Asp Ala Met Asp Arg Ile Phe Ala Arg Arg Tyr Asn Ala Thr
His Ile Lys Val Gly Gln Pro Gln Tyr Tyr Leu Ala Asn Gly Gly Phe
Leu Ile Ala Tyr Gln Pro Leu Leu Ser Asn Thr Leu Ala Glu Leu Tyr
```

FIG. 3-2

```
Val Arg Glu His Leu Arg Glu Gln Ser Arg Lys Pro Pro Asn Pro Thr
Pro Pro Pro Pro Gly Ala Ser Ala Asn Ala Ser Val Glu Arg Ile Lys
Thr Thr Ser Ser Ile Glu Phe Ala Arg Leu Gln Phe Thr Tyr Asn His
Ile Gln Arg His Val Asn Asp Met Leu Gly Arg Val Ala Ile Ala Trp
Cys Glu Leu Gln Asn His Glu Leu Thr Leu Trp Asn Glu Ala Arg Lys
Leu Asn Pro Asn Ala Ile Ala Ser Val Thr Val Gly Arg Arg Val Ser
Ala Arg Met Leu Gly Asp Val Met Ala Val Ser Thr Cys Val Pro Val
Ala Ala Asp Asn Val Ile Val Gln Asn Ser Met Arg Ile Ser Ser Arg
Pro Gly Ala Cys Tyr Ser Arg Pro Leu Val Ser Phe Arg Tyr Glu Asp
Gln Gly Pro Leu Val Glu Gly Gln Leu Gly Glu Asn Asn Glu Leu Arg
Leu Thr Arg Asp Ala Ile Glu Pro Cys Thr Val Gly His Arg Arg Tyr
Phe Thr Phe Gly Gly Gly Tyr Val Tyr Phe Glu Glu Tyr Ala Tyr Ser
His Gln Leu Ser Arg Ala Asp Ile Thr Thr Val Ser Thr Phe Ile Asp
Leu Asn Ile Thr Met Leu Glu Asp His Glu Phe Val Pro Leu Glu Val
Tyr Thr Arg His Glu Ile Lys Asp Ser Gly Leu Leu Asp Tyr Thr Glu
Val Gln Arg Arg Asn Gln Leu His Asp Leu Arg Phe Ala Asp Ile Asp
Thr Val Ile His Ala Asp Ala Asn Ala Ala Met Phe Ala Gly Leu Gly
Ala Phe Phe Glu Gly Met Gly Asp Leu Gly Arg Ala Val Gly Lys Val
Val Met Gly Ile Val Gly Gly Val Val Ser Ala Val Ser Gly Val Ser
Ser Phe Met Ser Asn Pro Phe Gly Ala Leu Ala Val Gly Leu Leu Val
Leu Ala Gly Leu Ala Ala Ala Phe Phe Ala Phe Arg Tyr Val Met Arg
Leu Gln Ser Asn Pro Met Lys Ala Leu Tyr Pro Leu Thr Thr Lys Glu
Leu Lys Asn Pro Thr Asn Pro Asp Ala Ser Gly Glu Gly Glu Glu Gly
Gly Asp Phe Asp Glu Ala Lys Leu Ala Glu Ala Arg Glu Met Ile Arg
Tyr Met Ala Leu Val Ser Ala Met Glu His Thr Glu His Lys Ala Lys
Lys Lys Gly Thr Ser Ala Leu Leu Ser Ala Lys Val Thr Asp Met Val
Met Arg Lys Arg Arg Asn Thr Asn Tyr Thr Gln Val Pro Asn Lys Asp
Ser Asp Ala Asp Glu Asp Asp Leu
```

FIG. 4-1

```
                                GAGTTGCGCCGCCCG           15
GACTGCAGCCGCCCGACCTCCGAAGGTCGTTACCGTTACCCGCCCGGCGTAT      67
ATCTCACGTACGACTCCGACTGTCCGCTGGTGGCCATCGTCGAGAGCGCCC      119
CGACGGCTGTATCGGCCCCCGGTCGGTCGTGGTCTACGACCGAGACGTTTTC     171
TCGATCCTCTACTCGGTCCTCCAGCACCTCGCCCCCAGGCTACCTGACGGGG     223
GGCACGACGGGCCCCCGTAGTCCCGCC ATG CGC CAG GGC GCC CCC GCG   271
CGG GGG TGC CGG TGG TTC GTC GTA TGG GCG CTC TTG GGG TTG ACG   316
CTG GGG GTC CTG GTG GCG TCG GCG GCT CCG AGT TCC CCG GCA CG   361
CCT GGG GTC GCG GCC GCG ACC CAG GCG GCG AAC GGG GGA CCT GCC   406
ACT CCG GCG CCG CCC GCC CCT GGC CCC GCC CCA ACG GGG GAC ACG   451
AAA CCG AAG AAG AAC AAA AAA CCG AAA AAC CCA CCG CCG CCG CGC   496
CCC GCC GGC GAC AAC GCG ACC GTC GCC GCG GGC CAC GCC ACC CTG   541
CGC GAG CAC CTG CGG GAC ATC AAG GCG AAG AAC ACC GAT GCA AAC   586
TTT TAC GTG TGC CCA CCC CCC ACG GGC GCC ACG GTG GTG CAG TTC   631
GAG CAG CCG CGC CGC TGC CCG ACC CGG CCC GAG GGT CAG AAC TAC   676
ACG GAG GGC ATC GCG GTG GTC TTC AAG GAG AAC ATC GCC CCG TAC   721
AAG TTC AAG GCC ACC ATG TAC TAC AAA GAC GTC ACC GTT TCG CAG   766
GTG TGG TTC GGC CAC CGC TAC TCC CAG TTT ATG GGG ATC TTT GAG   811
GAC CGC GCC CCC GTC CCC TTC GAG GAG GTG ATC GAC AAG ATC AAC   856
GCC AAG GGG GTC TGT CGG TCC ACG GCC AAG TAC GTG CGC AAC AAC   901
CTG GAG ACC ACC GCG TTT CAC CGG GAC GAC CAC GAG ACC GAC ATG   946
GAG CTG AAA CCG GCC AAC GCC GCG ACC CGC ACG AGC CGG GGC TGG   991
CAC ACC ACC GAC CTC AAG TAC AAC CCC TCG CGG GTG GAG GCG TTC  1036
CAC CGG TAC GGG ACG ACG GTA AAC TGC ATC GTC GAG GAG GTG GAC  1081
GCG CGC TCG GTG TAC CCG TAC AAC GAG TTT GTG CTG GCG ACT GGC  1126
GAC TTT GTG TAC ATG TCC CCG TTT TAC GGC TAC CGG GAG GGG TCG  1171
CAC ACC GAA CAC ACC AGC TAC GCC GCC GAC CGC TTC AAG CAG GTC  1216
GAC GGC TTC TAC GCG CGC GAC CTC ACC ACC AAG GCC GGG GCC ACG  1261
```

FIG. 4-2

| | |
|---|---|
| GCG CCG ACC ACC CGG AAC CTG CTC ACG ACC CCC AAG TTC ACC GTG | 1306 |
| GCC TGG GAC TGG GTG CCA AAG CGC CCG TCG GTC TGC ACC ATG ACC | 1351 |
| AAG TGG CAG GAG GTG GAC GAG ATG CTG CGC TCC GAG TAC GGC GGC | 1396 |
| TCC TTC CGA TTC TCC TCC GAC GCC ATA TCC ACC ACC TTC ACC ACC | 1441 |
| AAC CTG ACC GAG TAC CCG CTC TCG CGC GTG GAC CTG GGG GAC TGC | 1486 |
| ATC GGC AAG GAC GCC CGC GAC GCC ATG GAC CGC ATC TTC GCC CGC | 1531 |
| AGG TAC AAC GCG ACG CAC ATC AAG GTG GGC CAG CCG CAG TAC TAC | 1576 |
| CTG GCC AAT GGG GGC TTT CTG ATC GCG TAC CAG CCC CTT CTC AGC | 1621 |
| AAC ACG CTC GCG GAG CTG TAC GTG CGG GAA CAC CTC CGA GAG CAG | 1666 |
| AGC CGC AAG CCC CCA AAC CCC ACG CCC CCG CCG CCC GGG GCC AGC | 1711 |
| GCC AAC GCG TCC GTG GAG CGC ATC AAG ACC ACC TCC TCC ATC GAG | 1756 |
| TTC GCC CGG CTG CAG TTT ACG TAC AAC CAC ATA CAG CGC CAT GTC | 1801 |
| AAC GAT ATG TTG GGC CGC GTT GCC ATC GCG TGG TGC GAG CTG CAG | 1846 |
| AAT CAC GAG CTG ACC CTG TGG AAC GAG GCC CGC AAG CTG AAC CCC | 1891 |
| AAC GCC ATC GCC TCG GTC ACC GTG GGC CGG CGG GTG AGC GCG CGG | 1936 |
| ATG CTC GGC GAC GTG ATG GCC GTC TCC ACG TGC GTG CCG GTC GCC | 1981 |
| GCG GAC AAC GTG ATC GTC CAA AAC TCG ATG CGC ATC AGC TCG CGG | 2026 |
| CCC GGG GCC TGC TAC AGC CGC CCC CTG GTC AGC TTT CGG TAC GAA | 2071 |
| GAC CAG GGC CCG TTG GTC GAG GGG CAG CTG GGG GAG AAC AAC GAG | 2116 |
| CTG CGG CTG ACG CGC GAT GCG ATC GAG CCG TGC ACC GTG GGA CAC | 2161 |
| CGG CGC TAC TTC ACC TTC GGT GGG GGC TAC GTG TAC TTC GAG GAG | 2206 |
| TAC GCG TAC TCC CAC CAG CTG AGC CGC GCC GAC ATC ACC ACC GTC | 2251 |
| AGC ACC TTC ATC GAC CTC AAC ATC ACC ATG CTG GAG GAT CAC GAG | 2296 |
| TTT GTC CCC CTG GAG GTG TAC ACC CGC CAC GAG ATC AAG GAC AGC | 2341 |
| GGC CTG CTG GAC TAC ACG GAG GTC CAG CGC CGC AAC CAG CTG CAC | 2386 |
| GAC CTG CGC TTC GCC GAC ATC GAC ACG GTC ATC CAC GCC GAC GCC | 2431 |
| AAC GCC GCC ATG TTC GCG GGC CTG GGC GCG TTC TTC GAG GGG ATG | 2476 |
| GGC GAC CTG GGG CGT GCG GTC GGC AAG GTG GTG ATG GGC ATC GTG | 2521 |

FIG. 4-3

| | |
|---|---|
| GGC GGC GTG GTA TCG GCC GTG TCG GGC GTG TCC TCC TTC ATG TCC | 2566 |
| AAC CCC TTT GGG GCG CTG GCC GTG GGT CTG TTG GTC CTG GCC GGC | 2611 |
| CTG GCG GCG GCC TTC TTC GCC TTT CGC TAC GTC ATG CGG CTG CAG | 2656 |
| AGC AAC CCC ATG AAG GCC CTG TAC CCG CTA ACC ACC AAG GAG CTC | 2701 |
| AAG AAC CCC ACC AAC CCG GAC GCG TCC GGG GAG GGC GAG GAG GGC | 2746 |
| GGC GAC TTT GAC GAG GCC AAG CTA GCC GAG GCC CGG GAG ATG ATA | 2791 |
| CGG TAC ATG GCC CTG GTG TCG GCC ATG GAG CAC ACG GAA CAC AAG | 2836 |
| GCC AAG AAG AAG GGC ACG AGC GCG CTG CTT AGC GCC AAG GTC ACC | 2881 |
| GAC ATG GTC ATG CGC AAG CGC CGC AAC ACC AAC TAC ACC CAA GTT | 2926 |
| CCC AAC AAA GAC AGT GAC GCC GAC GAG GAC GAC CTG TGA CGGGGG | 2971 |

Stop (above TGA)

| | |
|---|---|
| GTTTGTTGTAAATAAAAACCACGGGTGTTAAACCGCATGCGCATCTTTTGGT | 3023 |
| TTTTTTTTTTGTACGCCCTTTGTGTGTGTGGGAAGAAAGAAAAAGGAACACA | 3075 |
| TAAACTCCCCCGGGTGTCCGCGGCCTGTTTCCTCTTTCCTTTCCCGTGACAA | 3127 |
| AACTGACCCCCTTGGTCAGTGCCGATTCCCCCCCCCCCCCCACGCCTTCCT | 3179 |
| CCACGTCGAAGGCTTTTGTATTGTAAAGCTACCCGCCTACCCGCGCCTCCCA | 3231 |
| ATAAAAAAAAAAAGAACATACACCAATGGGTCTTATTTGGTATTACCTGGTT | 3283 |
| TATTTAAAAAGATATACAGTAAGACATCCCATGGTACCAAAGACCGGGGCGA | 3335 |
| ATCAGCGGGCCCCCATCATCTGAGAGACGAACAAATCGGCGGCGCGGGCCGT | 3387 |
| GTCAACGTCCACGTGTGCTGCGCTGCTGGCGTTGACAAGGGCCCCGGCCTCC | 3439 |
| GCGTTGGATGCCTCCGGTTGGGATCC | 3465 |

FIG. 5-1

```
1-
GTCAACGGGCCCCTCTTTGATCACTCCACCACAGCTTCGCCCAGCCCCCAACACCGGCTGTATTACAGCGTCGAGAACGTGGGGCTCCTGCCGACC

101-
TGAAGGAGGAGCTCGCCCGGTCATCATGGGGCCGTCGGGTGCTGCTGATTGGGCCTCAGCGAATTAGAGGTTTACTGTTTGACGGCATTTC

201-
CGGAATAACGCCCACTCAGCGCCGCTGGCGATATATTCGGAGCTGATTATGCCACACTCTTTGCCTCGGTCTACCGTGCGGGAGCTCGAG

301-
TTGCGCCGCCCCGACTGAGCCGCCCCCGACCTCCGAAGTCGTTACCGTACCCCCGGTATATCTCAGTACGACTCCGACTGTCCGCTGGTGGCCA

401-
TCGTCGAGAGAGCGCCCCGACGGCTGTATCGGCCCCCGGTCGTGGTCTACGACGCCGAGTTTCTCGATCCTCTACTCGGTCCTCCAGCACCTCGC

501-
CCCCAGGCTACCTGACGGGGGCACGACGGGCCCCCGTAGTCCCGCC ATG CAC CAG GGC GCC CCC TCG TGG GGC CGG TGG TTC
                                                Met His Gln Gly Ala Pro Ser Trp Gly Arg Trp Phe-13

587-
GTC GTA TGG GCG CTC TTG GGG TTG ACG CTG GGG GTC CTG GTG GCG TCG GCG GCT CCG AGT TCC CCC GGC ACG CCT
Val Val Trp Ala Leu Leu Gly Leu Thr Leu Gly Val Leu Val Ala Ser Ala Ala Pro Ser Ser Pro Gly Thr Pro-38

662-
GGG GTC GCG CGC GAC CCA GGC GGA CGG GGG CCC TGC CAC TCC GGC GCC GCC CTT GGC GCC GCC CCA ACG
Gly Val Ala Arg Asp Pro Gly Gly Glu Arg Gly Pro Cys His Ser Gly Ala Ala Leu Gly Ala Ala Pro Thr-63

737-
GGG GAC CCG AAA CCG AAG AAG AAC AAA AAA CCG AAA AAC CCA ACG CCA CGC CCC GGC GAC AAC GCG ACC
Gly Asp Pro Lys Pro Lys Lys Asn Lys Lys Pro Lys Asn Pro Thr Pro Pro Arg Pro Ala Gly Asp Asn Ala Thr-88

812-
GTC GCC GCG GGC CAC GCC ACC CTG CGC GAC ATC AAG GCG GAG AAC ACC GAT GCA AAC TTT TAC
Val Ala Ala Gly His Ala Thr Leu Arg Asp Ile Lys Ala Glu Asn Thr Asp Ala Asn Phe Tyr-113

887-
GTG TGC CCA CCC CCC ACG GGC GCC ACG GTG GTG CAG TTC GAG CAG CCG CGC TGC CCG ACC CGG GAG GGT
Val Cys Pro Pro Pro Thr Gly Ala Thr Val Val Gln Phe Glu Gln Pro Arg Arg Cys Pro Thr Arg Glu Gly-138
```

FIG. 5-2

```
962-
CAG AAC TAC ACG GAG GGC ATC GCG GTG GTC TTC AAG GAG AAC ATC GCC CCG TAC AAG TTC AAG GCC ACC ATG TAC
Gln Asn Tyr Thr Glu Gly Ile Ala Val Val Phe Lys Glu Asn Ile Ala Pro Tyr Lys Phe Lys Ala Thr Met Tyr-163

1037-
TAC AAA GAC GTC ACC GTT TCG CAG GTG TGG TTC GAG TAC CAC CGC TCC CAG TTT ATG GGG ATC TTT GAG GAC CGC
Tyr Lys Asp Val Thr Val Ser Gln Val Trp Phe Glu Tyr His Arg Ser Gln Phe Met Gly Ile Phe Glu Asp Arg-188

1112-
GCC CCC GTC CCC TTC GAG GAG ATC AAC GAC AAG ATC AAC GCC GTC GTC TGT CGG TCC ACG GCC AAG TAC GTG
Ala Pro Val Pro Phe Glu Glu Val Ile Asn Asp Lys Ile Asn Ala Val Val Cys Arg Ser Thr Ala Lys Tyr Val-213

1187-
CGC AAC AAC CTG GAG ACC GCG TTT CAC CAC CGG GAC GAC CAC GAG ATG GAG CTG AAA CCG GCC AAC GCC
Arg Asn Asn Leu Glu Thr Ala Phe His Arg Asp Asp His Glu Thr Asp Met Glu Leu Lys Pro Ala Asn Ala-238

1262-
GCG ACC CGC AGC CGG GGC CAC TGG ACC ACC GAC CTC AAG TAC AAC CCC TCG CGG GTG GAG GCG TTC CAC CGG
Ala Thr Arg Ser Arg Gly His Trp Thr Thr Asp Leu Lys Tyr Asn Pro Ser Arg Val Glu Ala Phe His Arg-263

1337-
TAC GGG ACG ACG GTA AAC TGC ATC GTC GAG GAG GTG GAC GCG CGC TCG GTG TAC CCG TAC GAG TTT GTG CTG
Tyr Gly Thr Thr Val Asn Cys Ile Val Glu Glu Val Asp Ala Arg Ser Val Tyr Pro Tyr Asp Phe Val Leu-288

1412-
GCG ACT GGC GAC TTT GTG TAC ATG TAC TCC CCG TTT TAC GGC TAC CGG GAG CAC ACC AAG GAA CAC ACG TAC
Ala Thr Gly Asp Phe Val Tyr Met Tyr Ser Pro Phe Tyr Gly Tyr Arg Glu His Thr Lys Glu His Thr Tyr-313

1487-
GCC GCC GAC CGC TTC AAG CAG GTC GAC GCG CGG CGG CGC CGG CTC GCC AAG GCC CGG ACG GCG CCG
Ala Ala Asp Arg Phe Lys Gln Val Asp Arg Ala Arg Leu Thr Ala Lys Ala Thr Ala Pro-338

1562-
ACC ACC CGG AAC CTG CTC ACG GTG GCC TTC ACC CCC AAG TTC GAC TGG GTG GTG CCA AAG GCC TCG GTC TGC
Thr Thr Arg Asn Leu Leu Thr Val Ala Phe Thr Pro Lys Phe Asp Trp Val Ala Pro Lys Ala Ser Val Cys-363

1637-
ACC ATG ACC AAG TGG CAG GAA GTG GAC GAG ATG CTG CGC TCC GAG TAC CGC GGC TCC TTC CGA TTC TCC GAC
Thr Met Thr Lys Trp Gln Glu Val Asp Glu Met Leu Arg Ser Glu Tyr Arg Gly Ser Phe Arg Phe Ser Asp-388
```

Fig. 5-3

```
1712-
GCC ATA TCC ACC ACC TTC ACC AAC CTG ACC GAG TAC CCG CTC TCG CGC GTG GAC CTG GGG GAC TGC ATC GGC
Ala Ile Ser Thr Thr Phe Thr Asn Leu Thr Glu Tyr Pro Leu Ser Arg Val Asp Leu Gly Asp Cys Ile Gly-413

1787-
AAG GAC GCC CGC GAC ATG GAC GCC ATC TTC GCC CGC AGG AGG TAC AAC GCG ACG CAC ATC AAG GTG GGC CAG CCG
Lys Asp Ala Arg Asp Met Asp Ala Ile Phe Ala Arg Arg Tyr Asn Ala Thr His Ile Lys Val Gly Gln Pro-438

1862-
CAG TAC TAC CTG GCC AAT GGG GGC TTT CTG ATC GCG TAC CAG CCC CTT CTC AGC AAC ACG CTC GCG GAG CTG TAC
Gln Tyr Tyr Leu Ala Asn Gly Gly Phe Leu Ile Ala Tyr Gln Pro Leu Leu Ser Asn Thr Leu Ala Glu Leu Tyr-463

1937-
GTG CGG GAA CAC CTC CGA GAG CAG AGC CGC AAG CCC CCA AAC CCC ACG CCC CCG CCC GGG GCC AGC GCC AAC
Val Arg Glu His Leu Arg Glu Gln Ser Arg Lys Pro Pro Asn Pro Thr Pro Pro Pro Gly Ala Ser Ala Asn-488

2012-
GCG TCC GTG GAG CGC ATC AAG ACC TCC ATC GAG TTC GCC CGG CTG CAG TTT ACG TAC AAC CAC ATA CAG
Ala Ser Val Glu Arg Ile Lys Thr Ser Ile Glu Phe Ala Arg Leu Gln Phe Thr Tyr Asn His Ile Gln-513

2087-
CGC CAT GTC AAC GAT ATG TTG GGC CGC GTT GCC ATC GCG TGG TGC GAG CTA CAG AAT CAC GAG CTG ACC CTG TGG
Arg His Val Asn Asp Met Leu Gly Arg Val Ala Ile Ala Trp Cys Glu Leu Gln Asn His Glu Leu Thr Leu Trp-538

2162-
AAC GAG GCC CGG AAG CTG AAC CCC AAC GCC ATC GCC TCG GTC ACC GTG GGC CGG AGC GCG ATG CGG ATG CTC
Asn Glu Ala Arg Lys Leu Asn Pro Asn Ala Ile Ala Ser Val Thr Val Gly Arg Ser Ala Arg Met Leu-563

2237-
GGC GAC GTG ATG GCC CTG GTC TCC ACG TGC GTG CCG GTG CCC GCC GAC GTC CAA AAC TCG ATG CGC ATC
Gly Asp Val Met Ala Val Ser Thr Cys Val Pro Val Pro Ala Ala Asp Ile Val Gln Asn Ser Met Arg Ile-588

2312-
AGC TCG CGG CCC GCC TGC AGC TAC AGC CGC TTT CGG TAC GAA GAC CAG CGG CCG TTG GTC GAG
Ser Ser Arg Pro Gly Ala Cys Ser Tyr Ser Arg Phe Arg Tyr Glu Asp Gln Arg Pro Leu Val Glu-613

2387-
GGG CAG CTG GGG GAG GAG AAC AAC GAG CTG CGG CTG ACG TGC ATC GAG ACG GGA CAC CGG CGC
Gly Gln Leu Gly Glu Glu Asn Asn Glu Leu Arg Leu Thr Cys Ile Glu Pro Thr Val Gly His Arg Arg-638

2462-
TAC TTC ACC TTC GGT GGG GGC TAC TAC GTG TAC TTC GAG GAG TAC TCC CAC CAG CTG AGC CGC GCC GAC ATC
Tyr Phe Thr Phe Gly Gly Gly Tyr Tyr Val Tyr Phe Glu Glu Tyr Ser His Gln Leu Ser Arg Ala Asp Ile-663
```

Fig. 5-4

```
2537-
ACC ACC GTC AGC ACC TTC ATC GAC CTC AAC ATC ACC ATG CTG GAG GAT CAC GAG TTT GTC CCC CTG GAG GTG TAC
Thr Thr Val Ser Thr Phe Ile Asp Leu Asn Ile Thr Met Leu Glu Asp His Glu Phe Val Pro Leu Glu Val Tyr-688

2612-
ACC CGC CAC GAG ATC AAG GAC AGC GGC CTG CTG GAC TAC GAG GTC CAG CGC AAC CAG CGC CTG CAC GAC CTG
Thr Arg His Glu Ile Lys Asp Ser Gly Leu Leu Asp Tyr Thr Glu Val Gln Arg Asn Gln Arg Leu His Asp Leu-713

2687-
CGC TTC GCC GAC ATC GAC ACG GTC ATC CAC GCC AAC GCC GCC ATG TTC GCG GGC CTG GGC TTC TTC
Arg Phe Ala Asp Ile Asp Thr Val Ile His Ala Asn Ala Ala Met Phe Ala Gly Leu Gly Ala Phe Phe-738

2762-
GAG GGG ATG GGC GAC CTG GGG CGC GCG GTC AAG GTG GTG ATG GGA CTC GTG GGC GGC GTG GTA TCG GCG GTG
Glu Gly Met Gly Asp Leu Gly Arg Ala Val Lys Val Val Met Gly Leu Val Gly Gly Val Val Ser Ala Val-763

2837-
TCG GGC GTG TCC TCC ATG TCC AAC CCC TTT GGG GCG CTG TTG GTC CTG GCC GGC CTG GCG
Ser Gly Val Ser Ser Phe Met Ser Asn Pro Phe Gly Ala Leu Leu Val Leu Ala Gly Leu Ala-788

2912-
GCG GCC TTC TTC GCC TTT CGT TAC GTC ATG CGG CTG CAG AGC AAC CCC ATG AAG GCC CTG TAC CCT CTA ACC ACC
Ala Ala Phe Phe Ala Phe Arg Tyr Val Met Arg Leu Gln Ser Asn Pro Met Lys Ala Leu Tyr Pro Leu Thr Thr-813

2987-
AAG GAG CTC AAG AAC CCC ACC AAC CCG GAC GCG TCC GGG GAG GAG GGC GGC GGG GAC TTT GAC GAG GCC AAG
Lys Glu Leu Lys Asn Pro Thr Asn Pro Asp Ala Ser Gly Glu Glu Gly Gly Gly Asp Phe Asp Glu Ala Lys-838

3062-
CTA GCC GAG GCC AGG GAG ATG ATA CGG TAC ATG GCC CTG GTG TCG GCC ATG GAG CAC AAG GAA CGC AAG
Leu Ala Glu Ala Arg Glu Met Ile Arg Tyr Met Ala Leu Val Ser Ala Met Glu Arg Thr Glu His Lys Ala Lys-863

3137-
AAG AAG GGC ACG AGC CGG CTG CTC AGC GCC AAG GTC ATG CGC AAG CGC AAC ACC AAC TAC
Lys Lys Gly Thr Ser Arg Leu Leu Ser Ala Lys Val Thr Asp Met Val Met Arg Lys Arg Asn Thr Asn Tyr-888

3212-
ACC CAA GTT CCC AAC AAA GAC GGT GAC GCC GAC GAG GAC CTG TGACGGGGGGTTTGTTGTGTAAATAAAACCACGGGTGTTAA
Thr Gln Val Pro Asn Lys Asp Gly Asp Ala Asp Glu Asp Leu END

3297-
ACCGCATGCGATCTTTTGGTTTTTTGTTGGTCAGCCTTTGTGTGTGTGGAAGAAAAGGAACACATAACTCCCCCGGGTGTCCGGGGC
```

FIG. 5-5

```
3397-
CTGTTTCCTCTTCCTTTCCGTTGACAAACGGACCCCCTTGGTCAGTGCCGATTTCCTCCCCCCACGCCCTTCCTCCACGTCAAAGGCTTTTGCATTGT

3497-
AAAGCTACCCGCCTACCCGGCCCCCTCCCAATAAAAAAGAACATACACCAATGGTCTTATTGGTATTACCTGTTTATTTAAAAGATATACAGTA

3597-
AGACATCCCATGGTACCAAAGACCGGGGGCCGAATCAGCGGGGGCCCCCATCATCTGAGAGACGAACAAATCGGCGGGGCCGTGTCAACGTCCACGTGTG

3697-
CTGCGCTGCTGGGCGTTGACAAGGCCCCCGGCCTCCGGCGTTGGATGCTCCGGTTGGGATCC
```

Fig. 6-1

```
CTCGGAGAAGATGCTGCGGTCAGCGTCCACGGCGAGGTGCTGCCCGCGACGTTCGCCGCG    60

GTCGCCAACGGCTTTGCGGCCGCGCGCCGGCTTCTCGCCGCCCCTGACGGCGGGCGCGGG   120

CACGGTCATCGACAACCGCTCGGCGCCGGGCGTGTTCGACGCGCACCGGTTCATGCGAGC   180

GTCTCTCCTGCGACACCAGGTGGACCCGGCCCTGCTCCCCAGCATCACCCATCGCTTCTT   240

CGACTCGTCAACGGGCCCCTCTTTGATCACTCCACCCACAGCTTCGCCCAGCCCCCCAA    300

CACCGCGCTGTATTACAGCGTCGAGAACGTGGGGCTCCTGCCGCACCTGAAGGAGGAGCT   360

CGCCCGGTTCATCATGGGGGCGGGGGGCTCGGGTGCTGATTGGGCCGTCAGCGAATTTCA   420

GAGGTTTTACTGTTTTGACGGCATTTCCGGAATAACGCCCACTCAGCGCGCCGCCTGGCG   480

ATATATTCGCGAGCTGATTATCGCCACCACACTCTTTGCCTCGGTCTACCGGTGCGGGGA   540

GCTCGAGTTGCGCCGCCCGGACTGCAGCCGCCCGACCTCCGAAGGTCGTTACCGTTACCC   600

GCCCGGCGTATATCTCACGTACGACTCCGACTGTCCGCTGGTGGCCATCGTCGAGAGCGC   660

CCCCGACGGCTGTATCGGCCCCCGGTCGGTCGTGGTCTACGACCGAGACGTTTTCTCGAT   720

CCTCTACTCGGTCCTCCAGCACCTCGCCCCCAGGCTACCTGACGGGGGGCACGACGGGC    779
```

```
                MetArgGlnGlyAlaAlaArgGlyCysArgTrpPheValValTrp   -15
CCCCGTAGTCCCGCCATGCGCCAGGGCGCCGCGCGGGGGTGCCGGTGGTTCGTCGTATGG   839

AlaLeuLeuGlyLeuThrLeuGlyValLeuValAlaSerAlaAlaProSerSerProGly     6
GCGCTCTTGGGGTTGACGCTGGGGGTCCTGGTGGCGTCGGCGGCTCCGAGTTCCCCCGGC   899

ThrProGlyValAlaAlaAlaThrGlnAlaAlaAsnGlyGlyProAlaThrProAlaPro    26
ACGCCTGGGGTCGCGGCCGCGACCCAGGCGGCGAACGGGGGACCTGCCACTCCGGCGCCG   959

ProAlaProGlyProAlaProThrGlyAspThrLysProLysLysAsnLysLysProLys    46
CCCGCCCCTGGCCCCTCCCCAACGGGGGACACGAAACCGAAGAACAACAAAAAACCGAAA  1019

AsnProProProProArgProAlaGlyAspAsnAlaThrValAlaAlaGlyHisAlaThr    66
AACCCACCGCCGCCGCGCCCCGCCGGCGACAACGCGACCGTCGCCGCGGGCCACGCCACC  1079

LeuArgGluHisLeuArgAspIleLysAlaGluAsnThrAspAlaAsnPheTyrValCys    86
CTGCGCGAGCACCTGCGGGACATCAAGGCGGACAACACCGATGCAAACTTTTACGTGTGC  1139

ProProProThrGlyAlaThrValValGlnPheGluGlnProArgArgCysProThrArg   106
CCACCCCCCACGGGCGCCACGGTGGTGCAGTTCGACGAGCCGCGCCGCTGCCCGACCCGG  1199

ProGluGlyGlnAsnTyrThrGluGlyIleAlaValValPheLysGluAsnIleAlaPro   126
CCCGAGGGTCAGAACTACACGGAGGGCATCGCGGTGGTCTTCAAGGACAACATCGCCCCG  1259

TyrLysPheLysAlaThrMetTyrTyrLysAspValThrValSerGlnValTrpPheGly   146
TACAAGTTCAAGGCCACCATGTACTACAAAGACGTCACCGTTTCGCAGGTGTGGTTCGGC  1319

HisArgTyrSerGlnPheMetGlyIlePheGluAspArgAlaProValProPheGluGlu   166
CACCGCTACTCCCAGTTTATGGGGATCTTTGAGGACCGCGCCCCCGTCCCCTTCGAGGAG  1379

ValIleAspLysIleAsnAlaLysGlyValCysArgSerThrAlaLysTyrValArgAsn   186
GTGCTCGACAAGATCAACGCCAAGGGGGTCTGTCGGTCCACGGCCAAGTACGTGCGCAAC  1439
```

Fig. 6-2

```
AsnLeuGluThrThrAlaPheHisArgAspAspHisGluThrAspMetGluLeuLysPro      206
AACCTGGAGACCACCGCGTTTCACCGGGACGACCACGAGACCGACATGGAGCTGAAACCG     1499

AlaAsnAlaAlaThrArgThrSerArgGlyTrpHisThrThrAspLeuLysTyrAsnPro      226
GCCAACGCCGCGACCCGCACGAGCCGGGGCTGGCACACCACCGACCTCAAGTACAACCCC     1559

SerArgValGluAlaPheHisArgTyrGlyThrThrValAsnCysIleValGluGluVal      246
TCGCGGGTGGAGGCGTTCCACCGGTACGGGACGACGGTAAACTGCATCGTCGAGGAGGTG     1619

AspAlaArgSerValTyrProTyrAspGluPheValLeuAlaThrGlyAspPheValTyr      266
GACGCGCGCTCGGTGTACCCGTACGACGAGTTTGTGCTGGCGACTGGCGACTTTGTGTAC     1679

MetSerProPheTyrGlyTyrArgGluAlySerHisThrGluHisThrSerTyrAlaAla      286
ATGTCCCCGTTTTACGGCTACCGGGAGGGGTCGCAGACCGAACACACCAGCTACGCCGCC     1739

AspArgPheLysGlnValAspGlyPheTyrAlaArgAspLeuThrTyrLysAlaArgAla      306
GACCGCTTCAAGCAGGTTGACGGCTTCTACGCGCGCGACCTCACCACCAAGGCCCGGGCC     1799

ThrAlaProThrThrArgAsnLeuLeuThrThrProLysPheThrValAlaTrpAspTrp      326
ACGGCGCCGACCACCCGGAACCTGCTCACGACCCCCAAGTTCACCGTGGCCTGGGACTGG     1859

ValProLysArgProSerValCysThrMetThrLysTrpGlnGluValAspGluMetLeu      346
GTGCCAAAGCGCCCGTCGGTCTGCACCATGACCAAGTGGCAGGAGGTGGACGAGATGCTG     1919

ArgSerGluTyrGlyGlySerPheArgPheSerSerAspAlaIleSerThrThrPheThr      366
CGCTCCGAGTACGGCGGCTCCTTCCGATTCTCCTCCGACGCCATATCCACCACCTTCACC     1979

ThrAsnLeuThrGluTyrProLeuSerArgValAspLeuGlyAspCysIleGlyLysAsp      386
ACCAACCTGACCGAGTACCCGCTCTCGCGCGTGGACCTGGGGGACTGCATCGGCAAGGAC     2039

AlaArgAspAlaMetAspArgIlePheAlaArgArgTyrAsnAlaThrHisIleLysVal      406
GCCCGCGACGCCATGGACCGCATCTTCGCCCGCAGGTACAACGCGACGCACATCAAGGTG     2099

GlyGlnProGlnTyrTyrLeuAlaAsnGlyGlyPheLeuIleAlaTyrGlnProLeuLeu      426
GGCCAGCCGCAGTACTACCTGGCCAATGGGGGCTTTCTGATCGCGTACCAGCCCCTTCTC     2159

SerAsnThrLeuAlaGluLeuTyrValArgGluHisLeuArgGluGlnSerArgLysPro      446
AGCAACACGCTCGCGGAGCTGTACGTGCGGGAACACCTCCGAGAGCAGAGCCGCAAGCCC     2219

ProAsnProThrProProProProGlyAlaSerAlaAsnAlaSerValGluArgIleLys      466
CCAAACCCCACGCCCCCGCCGCCCGGGGCCAGCGCCAACGCGTCCGTGGAGCGCATCAAG     2279

ThrThrSerSerIleGluPheAlaArgLeuGlnPhrThrTyrAsnHisIleGlnArgHis      486
ACCACCTCCTCCATCGAGTTCGCCCGGCTGCAGTTTACGTACAACCACATACAGCGCCAT     2339

ValAsnAspMetLeuGlyArgValAlaIleAlaTrpCysGluLeuGlnAsnHisGluLeu      506
GTCAACGATATGTTGGGCCGCGTTGCCATCGCGTGGTGCGAGCTGCAGAATCACGAGCTG     2399

ThrLeuTrpAsnGluAlaArgLysLeuAsnProAsnAlaIleAlaSerAlaThrValGly      526
ACCCTGTGGAACGAGGCCCGCAAGCTGAACCCCAACGCCATCGCCTCGGCCACCGTGGGC     2459

ArgArgValSerAlaArgMetLeuGlyAspValMetAlaValSerThrCysValProVal      546
CGGCGGGTGAGCGCGCGGATGCTCGGCGACGTGATGGCCGTCTCCACGTGCGTGCCGGTC     2519

AlaAlaAspAsnValIleValGlnAsnSerMetArgIleSerSerArgProGlyAlaCys      566
GCCGCGGACAACGTGATCGTCCAAAACTCGATGCGCATCAGCTCGCGGCCCGGGCCTGC     2579

TyrSerArgProLeuValSerPheArgTyrGluAspGlnGlyProLeuValGluGlyGln      586
TACAGCCGCCCCCTGGTCAGCTTTCGGTACGAAGACCAGGGCCCGTTGGTCGAGCGGCAG     2639
```

Fig. 6-3

```
LeuGlyGluAsnAsnGluLeuArgLeuThrArgAspAlaIleGluProCysThrValGly     606
CTGGGGGAGAACAACGAGCTGCGGCTGACGCGCGATGCGATCGAGCCGTGCACCGTGGGA    2699

HisArgArgTyrPheThrPheGlyGlyGlyTyrValTyrPheGluGluTyrAlaTyrSer     626
CACCGGCGCTACTTCACCTTCGGCGGGGGCTACGTGTACTTCGAGGAGTACGCGTACTCC    2759

HisGlnLeuSerArgAlaAspIleThrThrValSerThrPheIleAspLeuAsnIleThr     646
CACCAGCTGAGCCGCGCCGACATCACCACCGTCAGCACCTTCATCGACCTCAACATCACC    2819

MetLeuGluAspHisGluPheValProLeuGluValTyrThrArgHisGluIleLysAsp    666
ATGCTGGAGGATCACGAGTTTGTCCCCCTGGAGGTGTACACCCGCCACGCGATCAAGGAC    2879

SerGlyLeuLeuAspTyrThrGluValGlnArgArgAsnGluLeuHisAspLeuArgPhe    686
AGCGGCCTGCTGGACTACACGGAGGTCCAGCGCCGCAACCAGCTGCACGACCTGCGCTTC    2939

AlaAspIleAspThrValIleHisAlaAspAlaAsnAlaAlaMetPheAlaGlyLeuGly    706
GCCGACATCGACACGGTCATCCACGCCGACGCCAACGCCGCCATGTTCGCGGGCCTGGGC    2999

AlaPhePheGluGlyMetGlyAspLeuGlyArgAlaValGlyLysValValMetGlyIle    726
GCGTTCTTCGAGGGGATGGGCGACCTGGGGCGCGCGGTCGGCAAGGTGGTGATGGGCATC    3059

ValGlyGlyValValSerAlaValSerGlyValSerSerPheMetSerAsnProPheGly    746
GTGGGCGGCGTGGTATCGGCCGTGTCGGGCGTGTCCTCCTTCATGTCCAACCCCTTTGGG    3119

AlaLeuAlaValGlyLeuLeuValLeuAlaGlyLeuAlaAlaAlaPhePheAlaPheArg    766
GCGCTGGCCGTGGGTCTGTTGGTCCTGGCCGGCCTGGCGGCGGCTTTCTTCGCCTTTCGC    3179

TyrValMetArgLeuGlnSerAsnProMetLysAlaLeuTyrProLeuThrThrLysGlu    786
TACGTCATGCGGCTGCAGAGCAACCCCATGAAGGCCCTGTACCCGCTAACCACCAAGGAG    3239

LeuLysAsnProThrAsnProAspAlaSerGlyGluGlyGluGluGlyGlyAspPheAsp    806
CTCAAGAACCCCACCAACCCGGACGCGTCCGGGGAGGGCGAGGAGGGCGGCGACTTTGAC    3299

GluAlaLysLeuAlaGluAlaArgGluMetIleArgTyrMetAlaLeuValSerAlaMet    826
GAGGCCAAGCTAGCCGAGGCCCGGGAGATGATACGGTACATGGCCCTGGTGTCTGCCATG    3359

GluArgThrGluHisLysAlaLysLysLysGlyThrSerAlaLeuLeuSerAlaLysVal    846
GAGCGCACGGAACACAAGGCCAAGAAGAAGGGCACGAGCGCGCTGCTCAGCGCCAAGGTC    3419

ThrAspMetValMetArgLysArgArgAsnThrAsnTyrThrGlnValProAsnLysAsp    866
ACCGACATGGTCATGCGCAAGCGCCGCAACACCAACTACACCCAAGTTCCCAACAAAGAC    3479

GlyAspAlaAspGluAspAspLeu                                         874
GGTGACGCCGACGAGGACGACCTGTGACGGGGGGTTTGTTGTAAATAAAAACCACGGGTG

TTAAACCGCATGTGCATCTTTTGGTTTGTTTGTTTGGTACGCCTTTTGTGTGTGTGGGAA    3599

GAAAGAAAAGGGAACACATAAACTCCCCCGGGTGTCCGCGGCCTGTTTCCTCTTTCCTTT

CCCGTGACAAAACGGACCCCCTTGGTCAGTGCCGATTCCCCCCCCACGCCTTCCTCCACG    3719

TCGAAGGCTTTTGCATTGTAAAGCTACCCGCCTACCCGCGCCTCCCAATAAAAAAAGAAC

ATACACCAATGGGTCTTATTTGGTATTACCTGGTTTATTTAAAAAGATATACAGTAAGAC    3839

ATCCCATGGTACCAAAGACCGGGGCGAATCAGCGGGCCCCCATCATCTGAGAGACGAACA
``` pHSG396SgD
| Xhol - Xbal
1.35 kb FRAGMENT
| Hinf I
0.91 kb FRAGMENT
— gD TERMINATOR ADAPTOR (12bp DNA FRAGMENT)
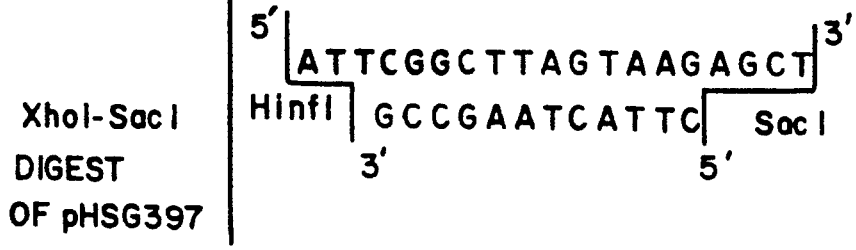
Xhol-SacI DIGEST OF pHSG397
pHSG397SgDΔHinf
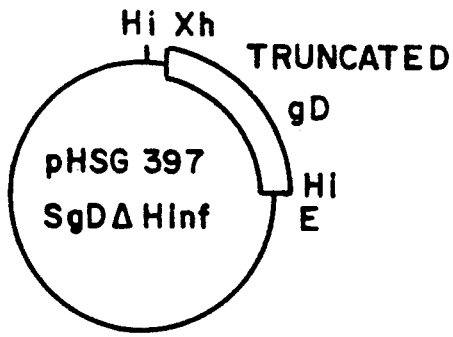
FIG. 8

Fig. 11

```
1    ATG GGG GGG GCT GCC GCC AGG TTG GGG GCC GTG ATT TTG TTT GTC
46   GTC ATA GTG GGC CTC CAT GGG GTC CGC GGC AAA TAT GCC TTG GCG
91   GAT GCC TCT CTC AAG ATG GCC GAC CCC AAT CGC TTT CGC GGC AAA
136  GAC CTT CCG GTC CTG GAC CCG CTG ACC GAC CCT CCG GGG GTC CGG
181  CGC GTG TAC CAC ATC CAG GCG GGC CTA CCG GAC CCG TTC CAG CCC
226  CCC AGC CTC CCG ATC ACG GTT TAC TAC GCC GTG TTG GAG CGC GCC
271  TGC CGC AGC GTG CTC CTA AAC GCA CCG TCG GAG GCC CCC CAG ATT
316  GTC CGC GGG GCC TCC GAA GAC GTC CGG AAA CAA CCC TAC AAC CTG
361  ACC ATC GCT TGG TTT CGG ATG GGA GGC AAC TGT GCT ATC CCC ATC
406  ACG GTC ATG GAG TAC ACC GAA TGC TCC TAC AAC AAG TCT CTG GGG
451  GCC TGT CCC ATC CGA ACG CAG CCC CGC TGG AAC TAC TAT GAC AGC
496  TTC AGC GCC GTC AGC GAG GAT AAC CTG GGG TTC CTG ATG CAC GCC
541  CCC GCG TTT GAG ACC GCC GGC ACG TAC CTG CGG CTC GTG AAG ATA
586  AAC GAC TGG ACG GAG ATT ACA CAG TTT ATC CTG GAG CAC CGA GCC
631  AAG GGC TCC TGT AAG TAC GCC CTC CCG CTG CGC ATC CCC CCG TCA
676  GCC TGC CTC TCC CCC CAG GCC TAC CAG CAG GGG GTG ACG GTG GAC
721  AGC ATC GGG ATG CTG CCC CGC TTC ATC CCC GAG AAC CAG CGC ACC
766  GTC GCC GTA TAC AGC TTG AAG ATC GCC GGG TGG CAC GGG CCC AAG
811  GCC CCA TAC ACG AGC ACC CTG CTG CCC CCT GAG CTG TCC GAG ACC
856  CCC AAC GCC ACG CAG CCA GAA CTC GCC CCG GAA GAC CCC GAG GAT
901  TCG CTA GCG CCT ACT TCA AGT TCT ACA AAG AAA ACA CAG CTA CAA
946  CTG GAG CAT TTA CTG CTG GAT TTA CAG ATG ATT TTG AAT GGA ATT
991  AAT AAT TAC AAG AAT CCC AAA CTC ACC AGG ATG CTC ACA TTT AAG
1036 TTT TAC ATG CCC AAG AAG GCC ACA GAA CTG AAA CAT CTT CAG TGT
1081 CTA GAA GAA GAA CTC AAA CCT CTG GAG GAA GTG CTA AAT TTA GCT
1126 CAA AGC AAA AAC TTT CAC TTA AGA CCC AGG GAC TTA ATC AGC AAT
1171 ATC AAC GTA ATA GTT CTG GAA CTA AAG GGA TCT GAA ACA ACA TTC
1216 ATG TGT GAA TAT GCT GAT GAG ACA GCA ACC ATT GTA GAA TTT CTG
1261 AAC AGA TGG ATT ACC TTT TGT CAA AGC ATC ATC TCA ACA CTG ACT
1306 TGA
```

Fig. 12

```
  1    Met Gly Gly Ala Ala Ala Arg Leu Gly Ala Val Ile Leu Phe Val
 16    Val Ile Val Gly Leu His Gly Val Arg Gly Lys Tyr Ala Leu Ala
 31    Asp Ala Ser Leu Lys Met Ala Asp Pro Asn Arg Phe Arg Gly Lys
 46    Asp Leu Pro Val Leu Asp Pro Leu Thr Asp Pro Pro Gly Val Arg
 61    Arg Val Tyr His Ile Gln Ala Gly Leu Pro Asp Pro Phe Gln Pro
 76    Pro Ser Leu Pro Ile Thr Val Tyr Tyr Ala Val Leu Glu Arg Ala
 91    Cys Arg Ser Val Leu Leu Asn Ala Pro Ser Glu Ala Pro Gln Ile
106    Val Arg Gly Ala Ser Glu Asp Val Arg Lys Gln Pro Tyr Asn Leu
121    Thr Ile Ala Trp Phe Arg Met Gly Gly Asn Cys Ala Ile Pro Ile
136    Thr Val Met Glu Tyr Thr Glu Cys Ser Tyr Asn Lys Ser Leu Gly
151    Ala Cys Pro Ile Arg Thr Gln Pro Arg Trp Asn Tyr Tyr Asp Ser
166    Phe Ser Ala Val Ser Glu Asp Asn Leu Gly Phe Leu Met His Ala
181    Pro Ala Phe Glu Thr Ala Gly Thr Tyr Leu Arg Leu Val Lys Ile
196    Asn Asp Trp Thr Glu Ile Thr Gln Phe Ile Leu Glu His Arg Ala
211    Lys Gly Ser Cys Lys Tyr Ala Leu Pro Leu Arg Ile Pro Pro Ser
226    Ala Cys Leu Ser Pro Gln Ala Tyr Gln Gln Gly Val Thr Val Asp
241    Ser Ile Gly Met Leu Pro Arg Phe Ile Pro Glu Asn Gln Arg Thr
256    Val Ala Val Tyr Ser Leu Lys Ile Ala Gly Trp His Gly Pro Lys
271    Ala Pro Tyr Thr Ser Thr Leu Leu Pro Pro Glu Leu Ser Glu Thr
286    Pro Asn Ala Thr Gln Pro Glu Leu Ala Pro Glu Asp Pro Glu Asp
301    Ser Leu Ala Pro Thr Ser Ser Thr Lys Lys Thr Gln Leu Gln
316    Leu Glu His Leu Leu Leu Asp Leu Gln Met Ile Leu Asn Gly Ile
331    Asn Asn Tyr Lys Asn Pro Lys Leu Thr Arg Met Leu Thr Phe Lys
346    Phe Tyr Met Pro Lys Lys Ala Thr Glu Leu Lys His Leu Gln Cys
361    Leu Glu Glu Glu Leu Lys Pro Leu Glu Glu Val Leu Asn Leu Ala
376    Gln Ser Lys Asn Phe His Leu Arg Pro Arg Asp Leu Ile Ser Asn
391    Ile Asn Val Ile Val Leu Glu Leu Lys Gly Ser Glu Thr Thr Phe
406    Met Cys Glu Tyr Ala Asp Glu Thr Ala Thr Ile Val Glu Phe Leu
421    Asn Arg Trp Ile Thr Phe Cys Gln Ser Ile Ile Ser Thr Leu Thr
```

FUSED PROTEINS COMPRISING GLYCOPROTEIN GD OF HSV-1 AND LTB

BACKGROUND OF THE INVENTION

The present invention relates to techniques for producing fused proteins useful as immunogens for therapeutic and preventive vaccines and techniques for bioactive fused protein useful for treatment of various diseases by expressing genes for fused proteins of heat-labile enterotoxin B subunit (LTB) and a protein heterologous to heat-labile enterotoxin (LT), using recombinant techniques.

Surfactants have been used for enhancing absorption of foreign or bioactive substances (proteins) through nasal mucosa tissues, and choleratoxin has been studied for the purpose of immunization with foreign antigens through nasal mucosa tissues. However, it has been desired to develop a protein which enhances the absorption of foreign or bioactive sustances through nasal mucosa tissues and which is suitable for the immunization through nasal mucosa tissues.

With the object of preparing an antigen suitable for the absorption and immunization of a foreign or bioactive protein through nasal mucosa tissues by targetting the foreign or bioactive protein topically, the present inventors have conducted investigations. As a result, the present inventors have discovered that fused protein obtained by combining LTB with a heterologous protein by genetic engineering techniques can attain this object.

SUMMARY OF THE INVENTION

Thus, the present invention relates to (1) a fused protein obtained by combining LTB with a protein heterologous to LT by genetic engineering techniques, (2) a recombinant DNA segment containing a nucleotide sequence coding for the fused protein described in (1), (3) a transformant harboring the recombinant DNA segment described in (2), (4) a method for producing the fused protein described in (1) which comprises cultivating the transformant described in (3), producing and accumulating the fused protein in a culture, and collecting the fused protein.

BRIEF DESCRIPTION OF THE DRAWINGS

FIG. 1 is a representation showing an example of an amino acid sequence of a surface protein gD gene of HSV-1 strain Miyama;

FIG. 2 is a representation showing an example of a nucleotide sequence corresponding to the amino acid sequence shown in FIG. 1;

FIG. 3 is a representation showing an example of an amino acid sequence of a surface protein gB gene of the HSV-1 strain Miyama;

FIG. 4 is a representation showing an example of a nucleotide sequence corresponding to the amino acid sequence shown in FIG. 3;

FIG. 5 shows an example of a nucleotide sequence of a surface protein gB of HSV-1 strain KOS, and an amino acid sequence deduced therefrom;

FIG. 6 shows an example of a nucleotide sequence of a surface protein of HSV-1 strain F, and an amino acid sequence deduced therefrom;

FIG. 8 is a schematic representation showing the construction of a truncated gD gene of HSV-1;

FIG. 11 is a schematic representation showing the construction of plasmid pHDTneol.

DESCRIPTION OF THE PREFERRED EMBODIMENTS

Figure 7:
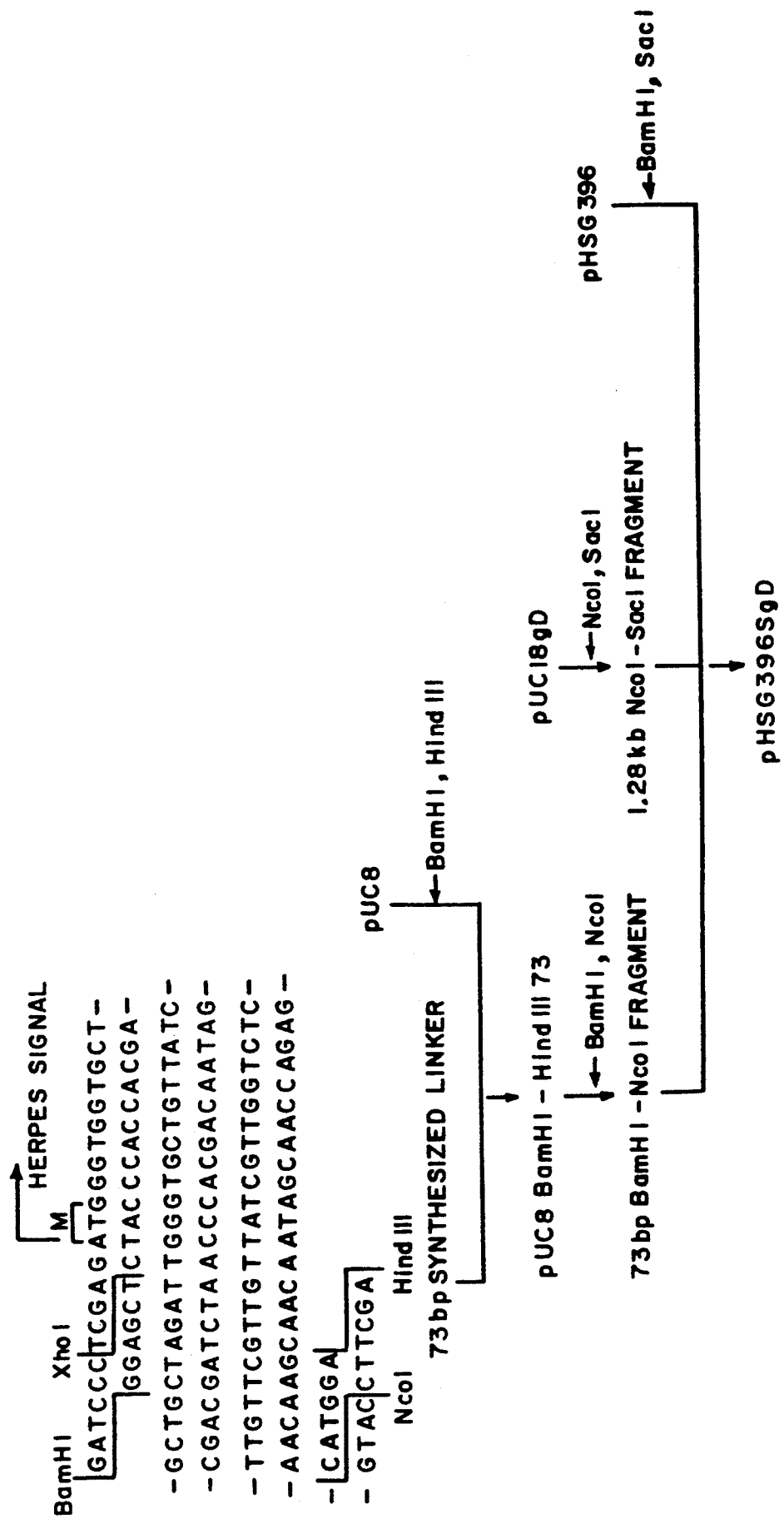
FIG. 7 is a schematic representation showing the construction of plasmid pHSG396SgD.

The fused protein comprises heat-labile enterotoxin B subunit (LTB) and a protein which is heterologous to heat-labile enterotoxin (heterologous protein).

The heterologous protein includes, for example, antigens (proteins or polypeptides) used for vaccines, and bioactive substances (proteins or polypeptides).

The antigens used for vaccines include antigens of viruses whose hosts are animals, such as antigens of herpesviruses including herpes simplex virus (HSV), varicella-zoster virus (VZV) and cytomegalovirus (CMV); antigens of retroviurses including human immunodeficiency virus (HIV) and adult T cell leukemia virus (HTLV-I); antigens of hepadonaviruses including hepatitis B virus (HBV); antigens of togaviruses including non-A, non-B hepatitis virus (HCV and HEV) and Japanese encephalitis virus; antigens of picornaviruses including hepatitis A virus (HAV); antigens of orthomyxoviruses including influenza virus; antigens of parvoviruses, antigens of papovaviruses; antigens of adenoviruses; antigens of poxviruses; antigens of reoviruses; antigens of paramyxoviruses; antigens of rhabdoviruses; antigens of arenaviruses; and antigens of coronaviruses; antigens of pathogenic protozoa such as a malarial antigen; and antigens of pathogenic protozoa such as a malarial antigen; and antigens of pathogenic bacteria such as a Bordetella pertussis antigen.

The bioactive substances include (e.g. an animal other than human, a plant or a microorganism) foreign or human-derived bioactive peptides and proteins such as hormones including insulin, human growth hormone, gonadotropin, inhibin, prolactin; enzymes including serratiopeptidase; cytokines including interferon (IFN), IFN-α, IFN-β, IFN-γ, interleukin (IL), IL-1, IL-2, IL-3, IL-4, IL-5, IL-6, IL-7, granular colony stimulating factor, granular macrophage colony stimulating factor, macrophage colony stimulating factor and erythropoietin; and growth factors including basic fibloblast growth factor and epidermal cell growth factor.

In some embodiments of the present invention, the protein heterologous to heat-labile enterotoxin may be fused with heat-labile enterotoxin through a linker. Linkers for use in the present invention can comprise one amino acid residue or a peptide residue comprising 2 to about 30 amino acid residues (preferably one amino acid residue or a peptide chain comprising 2 to about 10 amino acid residues) selected from G, A, V, L, I, S, T, C, M, E, D, K, R, H, F, Y, W, P, N and Q.

As an example of one of the many fused proteins disclosed herein, a fused protein of an HSV surface protein which is an HSV antigen with LTB will hereinafter be described. As the HSV surface protein, glycoproteins gD and gB lacking transmembrane domains are advantageously used.

Preferably, in accordance with the present invention, there are provided (1) a fused protein obtained by combining gD lacking transmembrane domain with LTB (I), or a fused protein obtained by combining gB lacking transmembrane domain with LTB (II); (2) a recombinant DNA containing a nucleotide sequence coding for the fused protein (I) or (II) (III or IV, respectively); (3) a transformant harboring the recombinant DNA (III) or (IV); (4) a method for producing the fused protein (I) or (II) which comprises cultivating the transformant harboring the recombinant DNA (III) or (IV), producing and accumulating the fused protein (I) or (II) in a culture, and collecting the fused protein.

As surface protein genes of HSV, there can be used, for example, gD and gB genes of various HSV-1 strains such as HSV-1 strain Miyama. Antigenic fragments of the proteins expressed by such genes are also included. Examples of the gD include a polypeptide having the amino acid sequence shown in FIG. 1 (surface protein gD of HSV-1 strain Miyama, Japanese Patent Application No. 63-180114/1988). The essential portion of this amino acid sequence is from Lys of No. 26 to Ala of No. 302. Examples of the DNAs containing the nucleotide sequence coding for this gD gene include a DNA having a nucleotide sequence corresponding to the nucleotide sequence shown in FIG. 2. The portion from No. 186 to No. 1016 thereof corresponds to the essential portion. Examples of the gB include a polypeptide having the amino acid sequence shown in FIG. 3 (surface protein gB of HSV-1 strain Miyama, Japanese Patent Application No. 1-158238/1989 filed on Jun. 22, 1989 and Japanese Patent Application No. 1-308941/1989 filed on Nov. 30, 1989). The essential portion thereof is from Ala of No. 1 to Asp of No. 293. Examples of the DNAs containing the nucleotide sequence coding for this gB gene include a DNA having a nucleotide sequence corresponding to the nucleotide sequence shown in FIG. 4. The portion from No. 341 to No. 1219 thereof corresponds to the essential portion. As used herein corresponding to permits, additions, deletions and substitutions of nucleotides may be made so long as the protein produced by the gene will still by functional.

The gB genes further include, for example, genes having the nucleotide sequences and the amino acid sequences deduced therefrom shown in FIG. 5 [surface protein gB of HSV-1 strain KOS, D. J. Bzik et al., *Virology*, 133, 301 (1984)] and FIG. 6 [surface protein gB of HSV-1 strain F, P. E. Pellet et al., *J. Virol.*, 53, 243 (1985)]. The LTB genes are combined with these genes, preferably with the truncated gD or gB gene lacking the coding regions of the transmembrane domains, whereby the fused protein genes can be constructed.

Any LTB gene can be used as long as it codes for an LTB active substance, and includes functional fragment thereof. The LTB active substance may be any LTB as long as it has LTB activity, namely the adjuvant activity. Examples of such substances include natural LTB produced in enterotoxigenic *Escherichia coli* separated from humans or pigs, recombinant LTB produced by recombinant technology and their related substances. In particular, B subunit (LThB) of LT produced in enterotoxigenic *E. coli* separated from humans (LTh) is preferable. When the LTB described above and the related substances thereof are proteins, they may have sugar chains or not.

As DNAs coding for LTB used for the present invention, there can be used any DNA segment coding for LTB produced by enterotoxigenic *E. coli*. The DNAs may be natural ones or synthetic ones, and may be a LTB gene or a portion thereof.

A DNA segment coding for LTB used for the present invention, for example, may be prepared from plasmid pJYL2299 containing LTh gene [T. Yamamoto and T. Yokota, *J. Bacteriol.*, 143, 652 (1980)] using appropriate restriction enzymes. DNAs coding for LThB may be prepared in large amount by amplification of the subcloning plasmid in E. coli.

The recombinant DNA segment (expression plasmid) containing the nucleotide sequence coding for the fused protein (I) or (II) of the present invention can be prepared, for example, by the following processes.

(a) A desired truncated gene is cut out from a plasmid in which the gD or gB gene of HSV-1 strain Miyama has been cloned. It can also be chemically synthesized.

(b) An appropriate linker is added thereto as needed, followed by construction of a fused gene in which an LTB gene is linked to the 3'-terminal portion of the DNA.

(c) The resulting fused protein gene is ligated downstream from a promoter in an expression vector.

In the present invention, any vector (for example, plasmid) may be used as long as it can be replicated in an eucaryotic cell as a host. When the host is yeast, examples of such vectors include pSH19 [S. Harashima et al., *Mol. Cell. Biol.,* 4. 771 (1984)] and pSH19-1 (European Patent Publication No. 0235430), and a vehicle for expression of foreign genes is obtained by inserting a promoter therein. When the host is an animal cell, the vehicle for expression of foreign genes is obtained, for example, by inserting an SV40-derived promoter, a retrovirus promoter or the like in pBR322.

As the promoter used in the present invention, any promoter is usable as long as the promoter is suitable for expression in the host used for the gene expression. When the host is yeast, it is preferred that a GLD (GAPDH) promoter, a PH05 promoter, a PGK promoter, an ADH promoter, a PH081 promoter and the like are used. When the host is an animal cell, an SV40-derived promoter, a retrovirus promoter and the like are preferably used.

The promoters can be prepared enzymatically from the corresponding genes. They can also be chemically synthesized.

By using the vector containing the recombinant DNA thus constructed, the eucaryotic cell is transformed.

The host includes, for example, yeast and animal cells.

Examples of the yeast include *Saccharomyces cerevisiae* AH22R$^-$, NA87-11A and DKD-5D and *Schizosaccharomyces pombe* ATCC38399(h$^-$ leul-32) and TH168(h$^{90}$ ade6-M210 ural leul) [M. Kishida and C. Shimada, *Current Genetics,* 10, 443(1986)]. Examples of the animal cells include adherent cells such as monkey COS-7 cell, monkey Vero cell, Chinese hamster ovary (CHO) cell, mouse L cell and human FL cell, and non-adherent cells such as mouse myeloma cell (such as SP2/0), mouse YAC-1 cell, mouse MethA cell, mouse P388 cell and mouse EL-4 cell.

The transformation of the yeast is carried out according to, for example, the method described in *Proc. Natl. Acad. Sci. U.S.A.,* 75, 1929 (1978). The transformation of the animal cell is carried out according to, for example, the method described in *Virology,* 52, 456 (1973).

The transformants (recombinants) thus obtained are cultivated by per se known methods.

When the transformants in which the host is yeast are cultivated, there is used, for example, Burkholder minimum medium [K. L. Bostian et al., *Proc. Natl. Acad. Sci. U.S.A.*, 77, 4505 (1980)] as a medium. The pH of the medium is preferably adjusted to about 5 to 8. The cultivation is usually carried out at about 20° to 35° C. for about 24 to 72 hours, with aeration or agitation if necessary.

When the transformants in which the host is an animal cell are cultivated, there can be used as the medium, for example, about 5 to 20% fetal calf serum-containing MEM medium [*Science*, 122, 501 (1952)], DMEM medium [*Virology*, 8, 396 (1959)], RPMI1640 medium [*The Journal of the American Medical Association*, 199, 519 (1967)]and 199 medium [*Proceeding of the Society for the Biological Medicine*, 73, 1 (1950)]. The pH is preferably about 6 to 8. The cultivation is usually carried out at about 30° to 40° C. for about 15 to 60 hours, with aeration or agitation if necessary.

In the present invention, the fused proteins having both the HSV surface antigenicity and the LTB activity can be separated and purified by appropriate combinations of per se known separating and purifying methods. These known separating and purifying methods include methods utilizing a solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse-phase high performance liquid chromatography and methods utilizing a difference in isoelectric point such as isoelectro focusing electrophoresis.

For the separation of fused proteins having both the HSV surface antigenicity and the LTB activity, a combination of ion-exchange chromatography and gel permeation chromatography. As fillers for ion exchange chromatography, cationic exchange resins using a sulfogroup as an exchanging group such as ST-Toyopearl 650 M (Toyo Soda, Japan) are preferable. Sovents for equilibriation of columns include 20 mM phosphate buffer (pH 5.8), and eluate solvents include 20 mM phosphate buffer containing 0 to 1M NaCl (pH 5.8). As fillers for gel permeation chromatography, porous particles such as Sephacryl S-300HR (TM) which may isolate a protein of about $1\times10^4$ to $5\times10^6$ molecular weight, are preferable. As solvents for gel permeation chromatography, 5 to 20 mM phosphate buffer containing 0.5 to 1.5 % NaCl (pH 6.8 to 7.2) is preferable. The fused protein can be purified as described above so that it is substantially free of contaminants. This fused protein can then be administered therapeutically.

The fused protein of a heterologous protein other than HSV surface antigen protein and LTB can be prepared using a gene (DNA) coding for that heterologous protein in lieu of the HSV surface antigen protein gene, according to the methods described above.

The antigen protein-LTB fused proteins and bioactive protein-LTB fused proteins are remarkably efficient for targetting to nasal mucosa tissues as compared with unfused proteins. LTB has not only binding activity specific to glycolipids on mucosal epidermal cell membranes but also activity to enhance the abosorption of a coexistent protein through mucosal tissues. The activity increases in case that LTB is fused with an objective protein. As a result, the antigen protein-LTB fused protein can induce immune response efficiently through nasal mucosa tissues, and the bioactive protein-LTB can enhance the absorption of the bioactive protein through nasal mucosa tissues.

The antigen protein-LTB fused protein can be administered pernasally as well as intramuscularly, subcutaneously or intracutaneously, as vaccines for prevention or treatment of infection of viruses, pathogenic protozoas or pathogenic bacteria. The bioactive protein-LTB fused protein can be administered pernasally. The per vaginam administration of an HSV antigen-LTB fused protein is also efficient. One would administer a therapeutically effective amount of the fused protein. This can be determined empirically. Typical dosages would range from 1 μg to 1 mg per body.

When bases, amino acids and so on are indicated by the abbreviations in this specification and the drawings, the abbreviations adopted by IUPAC-IUB Commission on Biochemical Nomenclature or commonly used in the art are employed. For example, the following abbreviations are used. When the optical isomer is capable of existing with respect to the amino acids, the L-form is represented unless otherwise specified.

DNA: Deoxyribonucleic acid
A: Adenine
T: Thymine
G: Guanine
C: Cytosine
SDS: Sodium dodecyl sulfate
Gly: Glycine (G)
Ala: Alanine (A)
Val: Valine (V)
Leu: Leucine (L)
Ile: Isoleucine (I)
Ser: Serine (S)
Thr: Threonine (T)
Cys: Cysteine (C)
½ Cys: Half Cycteine
Met: Methionine (M)
Glu: Glutamic acid (E)
Asp: Aspartic acid (D)
Lys: Lysine (K)
Arg: Arginine (R)
His: Histidine (H)
Phe: Phenylalanine (F)
Tyr: Tyrosine (Y)
Trp: Tryptophan (W)
Pro: Proline (P)
Asn: Asparagine (N)
Gln: Glutamine (Q)
$Ap^r$: Ampicillin-resistant gene
$Tc^r$: Tetracycline-resistant gene With respect to the proteins of the present invention, a portion of the amino acid sequence may be modified, namely there may be addition, elimination or substitution by a different amino acid(s). Furthermore, functional fragments of the proteins may also be used.

The present invention will hereinafter be described in detail with the following Reference Examples and Examples. It is understood of course that these Reference Examples and Examples are merely illustrative and are not intended to limit the scope of the invention.

Transformant CHO-HDT-2-35 obtained in Example 6 described below and harboring plasmid pHDTdhfr2 was deposited with the Fermentation Research Institute, Agency of Industrial Science and Technology, Ministry of International Trade and Industry, Japan (FRI) under the accession number FERM BP-2590 on Sep. 8, 1989. This microorganism was also deposited with the Institute for Fermentation, Osaka, Japan (IFO) under the accession number IFO 50209 on Aug. 24, 1989.

Trasformant Sp-neo-HDT-13-71 obtained in Example 8 described below and harboring plasmid pHDTneol was deposited with the FRI under the accession number FERM BP-3071 on Aug. 17, 1990. This microorganism was also deposited with the Institute for Fermentation, Osaka, Japan (IFO) under the accession number IFO 50254 on Aug. 8, 1990.

Transformant *Escherichia coli* DH1/pHSD BJ-1 harboring plasmid pHSD BJ-1 described in Reference Example mentioned below was deposited with the FRI under the accession number FERM BP-1784 on Mar. 9, 1988. This microorganism was also deposited with the IFO under the accession number IFO 14730 on FIG. 23, 1988.

REFERENCE EXAMPLE 1

Preparation of Plasmid pHSG396SgD (FIG. 7)

A DNA coding for the 20 amino acid residues from the N-terminus of gD, namely the 73-bp DNA fragment shown in FIG. 7 was chemically synthesized, and inserted into vector pUC8 digested with BamHI and HindIII.

The resulting pUC8 and BamHI-HindIII73 was digested with BamHI and NcoI to obtain a 73-bp fragment. On the other hand, a NcoI-SacI DNA fragment of about 1.28 kb was obtained from cloning plasmid pUC18gD having an HindIII-NruI fragment [plasmid pHSD BJ-1 (IFO 14730, FERM BP-1784 origin] of about 1.4 kb containing the gD-coding region of HSV. The above 73-bp fragment and the above NcoI-SacI DNA fragment were reacted with a BamHI-SacI digest of plasmid vector pHSG396 (Takara Shuzo) to prepare subcloning plasmid pHSG396SgD.

REFERENCE EXAMPLE 2

Construction of HSV-1 Truncated gD Gene (FIG. 8)

The plasmid vector pHSG396SgD (Reference Example 1) having the HSV-1 strain Miyama gD gene was digested with restriction enzymes XhoI and XbaI to obtain a DNA fragment of about 1.35 kb, followed by further digestion with restriction enzyme HinfI to obtain an XhoI-HinfI fragment of about 0.91 kb. A 12-bp DNA fragment shown in FIG. 8 containing a stop codon was chemically synthesized, and reacted with the above XhoI-HinfI fragment and an XhoI-SacI digest of plasmid vector pHSG397 (Takara Shuzo) to prepare subcloning plasmid pHSG397SgDΔHinf.

EXAMPLE 1

Figure 9:
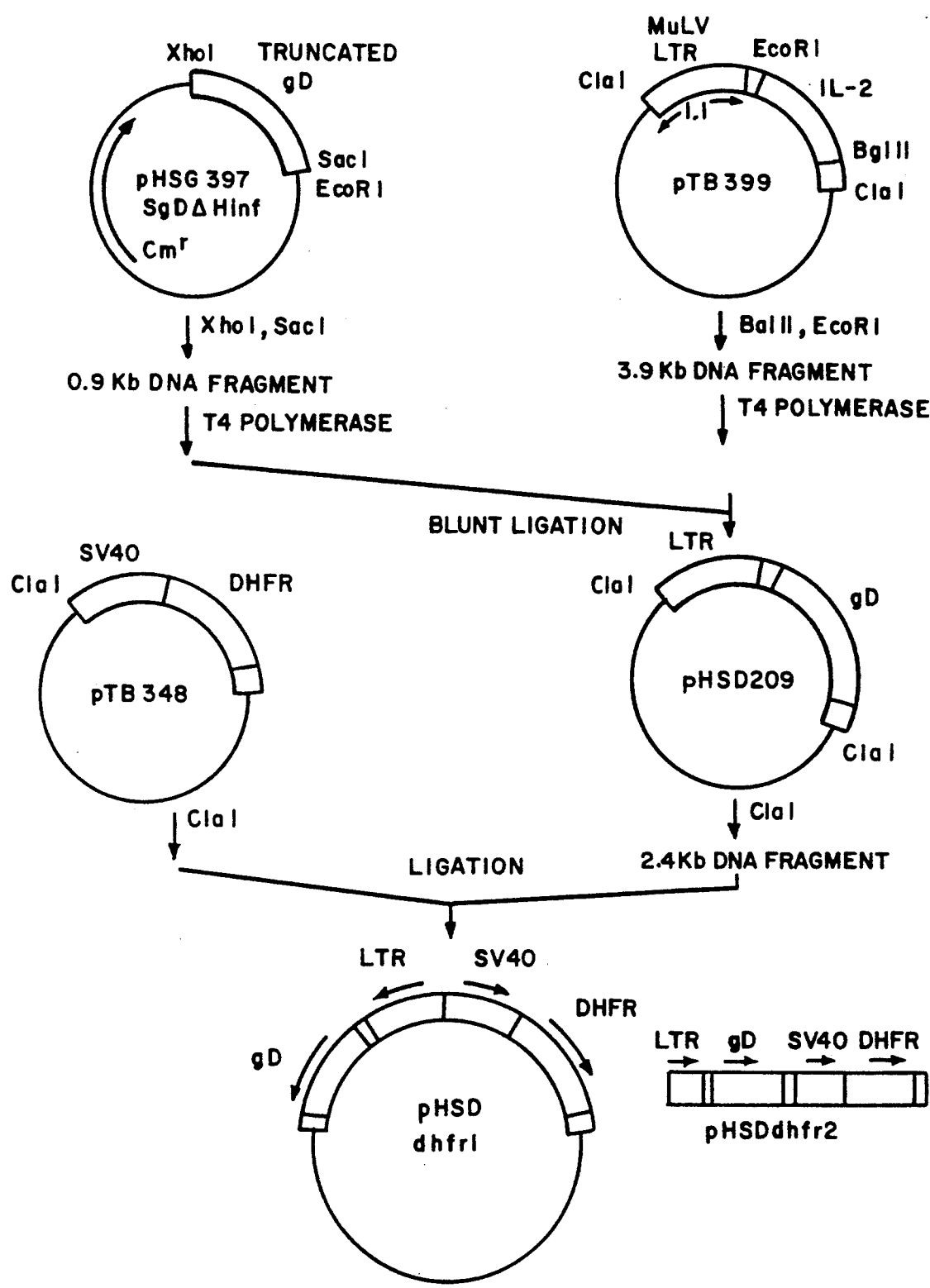
FIG. 9 is a schematic representation showing the construction of an expression plasmid for animal cells of the truncated gD gene of HSV-1.

Construction of Gene Expression Plasmid in Animal Cells for HSV-1 Trucated gD Gene (FIG. 9)

The plasmid pHSG397SgDΔHinf shown in Reference Example 2 was digested with restriction enzymes XhoI and SacI, and then T4 DNA polymerase was allowed to react on the digest to obtain a fragment of about 0.9 kb containing the truncated gD gene, both ends of the fragment being flush.

Then, plasmid pTB399 [Japanese Patent Unexamined Publication No. 61-63282/1986; R. Sasada et al., *Cell Structure and Function*, 12, 205 (1987)] was digested with restriction enzymes EcoRI and BglII, and then T4 DNA polymerase was allowed to react on the digest to obtain a fragment of about 3.9 kg both ends of which are flush. The resulting fragment was reacted with the above fragment containing truncated gD in the presence of T4 DNA ligase to obtain expression plasmid pHSD209.

Then, in order to express the gene stably in CHO cells and to enable gene amplification, a fragment of about 2.4 kb which was obtained by digesting the plasmid pHSD209 with restriction enzyme ClaI was inserted into the ClaI site of plasmid pTB348 (refer to Japanese Patent Unexamined Publication No. 61-63282/1986) to obtain plasmids pHSDdhfr1 and pHSDdhfr2.

EXAMPLE 2

Gene Expression of Truncated gD in Animal Cell

Using the plasmid pHSDdhfr1 constructed in Example 1, CHO cell DHFR− strain [G. Urlaub and L. A. Chasim, *Proc. Natl. Acad. Sci. U.S.A.*, 77, 4216–4220 (1980)] was transformed by the calcium phosphate method [C. M. Gorman et al, *Science*, 221, 551–553 (1983)] to obtain a transformant which was converted to DHFR+.

The resulting transformant CHO-HSD-1-7 was cultivated in Dulbecco MEM medium (Gibco) containing 10% fetal calf serum (Whittaker M. A. Bioproducts) so as to become confluent. Then, the medium was exchanged for a methionine-free medium, and 25 μCi/ml of $^{35}$S-methionine was added thereto, followed by cultivation overnight.

After a supernatant of the culture was recovered, 5 μl/ml of supernatant of rabbit anti-HSV-1 (MacIntyre) serum (Dakopatt) was added and the mixture was incubated at 4° C. for 2 hours. Protein-A-Sepharose (Pharmacia) was added to the mixture, followed by incubation at 4° C. for 2 hours, and by centrifugation to recover a precipitate. The precipitate was washed with a buffer containing 0.05% NP-40, and Laemmli buffer was added thereto, followed by heating at 100° C. for 5 minutes. After cooling, a supernatant was recovered by centrifugation and subjected to SDS-polyacrylamide gel electrophoresis. After electrophoresis, the gel was dried, and subjected to autoradiography. As a result, it was revealed that products of about 43 to 30 k daltons which were reactive to anti-HSV-1 was produced.

EXAMPLE 3

Purification of HSV-1 Truncated gD (t-gD) Expressed in Animal Cell 1.8 liter of the culture solution of CHO-HSD-1-7 strain cultivated by the method described in Example 2 was dialyzed against 36.0 liter of buffer (pH 8.0) containing 20 mM Tris at 2° C., for 16 hours. 336 g of ammonium sulfate was added gradually to 2 liter of the dialyzed solution and the mixture was stirred at 4° C. for 2 hours.

The resulting solution was applied onto a Butyl-Toyopearl column (Toyo Soda Co. Ltd. Japan) equilibrated with 168 g/l ammonium sulfate-20 mM Tris bufer (pH 8.0), and then the column was washed with 1.0 liter of the same buffer. Subsequently, t-gD was eluted with a linear gradient (600 ml) from 168 g/l of ammonium sulfate - 20 mM Tris buffer (pH 8.0) to 20 mM Tris buffer (pH 8.0). About 140 ml of the eluate containing t-gD was concentrated to 14 ml using Centriprep 10 (Amicon, U.S.A.).

The truncated gD fraction purified with the above Butyl-Toyopearl column was dialyzed against distilled water, followed by filtration for sterilization to obtain 14 ml of a purified truncated gD sample (536 μg/ml).

EXAMPLE 4

Characterization of HSV-1 Truncated gD Purified from Animal Cell

The following property of the purified truncated gD sample obtained in Example 3 was assayed.

The sample was subjected to SDS-polyacrylamide slab electrophoresis according to Laemmli's method [*Nature*, 227, 680 (1970)], and then to silver staining. As a result, the truncated gD protein was composed of molecules from 43,000 daltons to 30,000 daltons.

EXAMPLE 5

Figure 10:
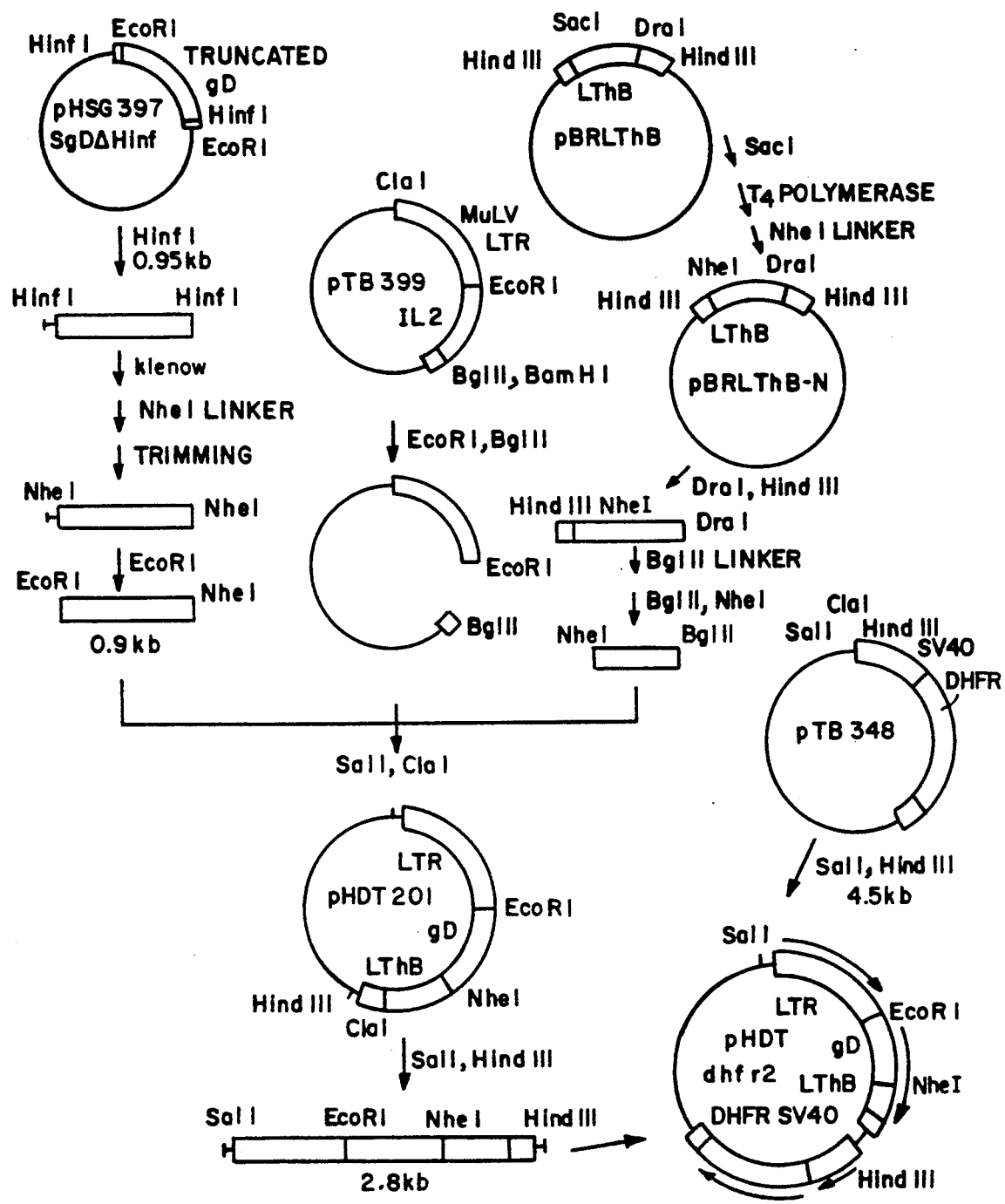
FIG. 10 is a schematic representation showing the construction of an expression plasmid of a fused protein gene according to the present invention.
Figure 13:
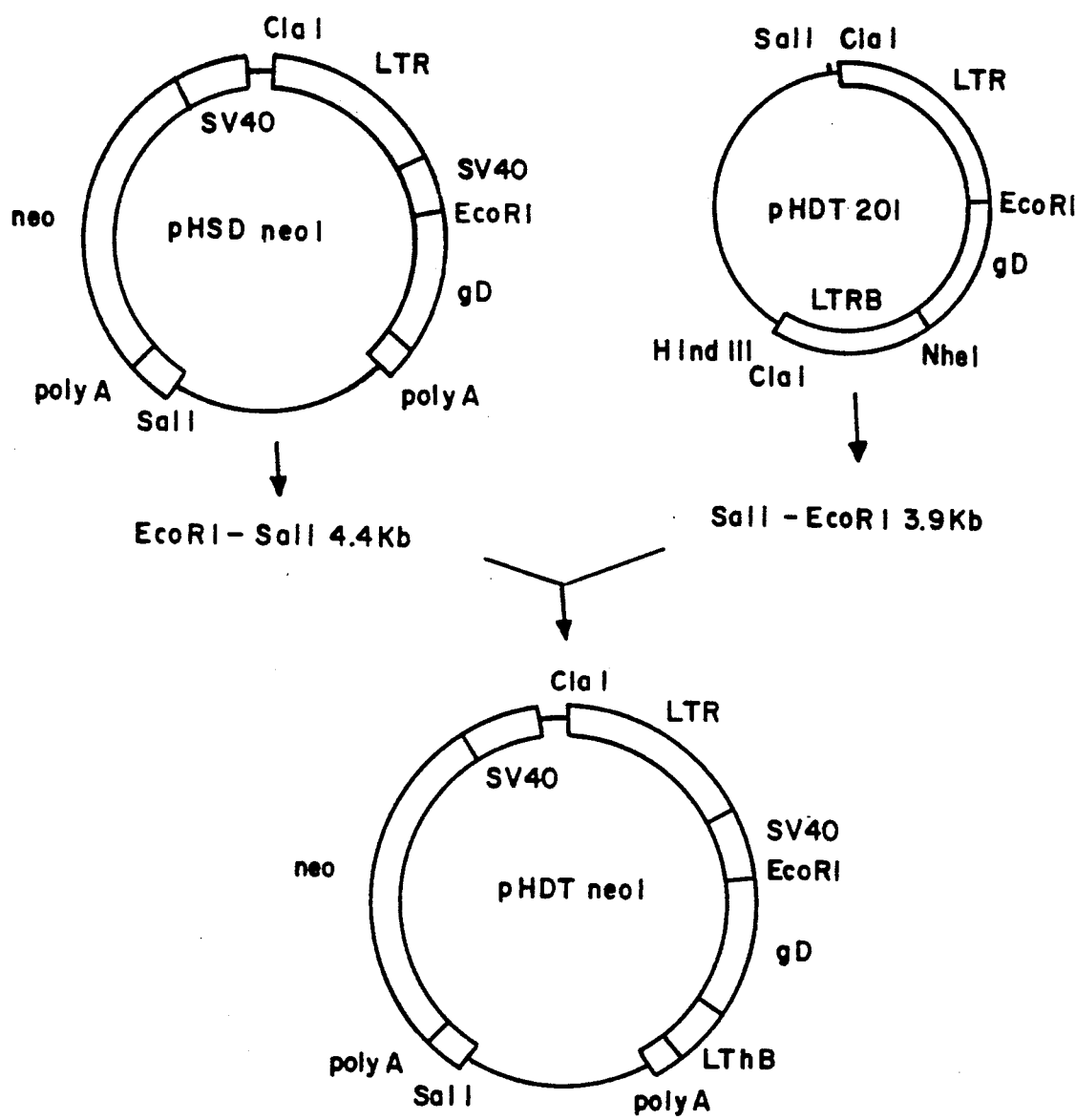

Construction of Gene Expression Plasmid for Fused Protein Composed of HSV-1 truncated gD and LThB (FIG. 10)

pHSG397SgDΔHinf described in Reference Example 2 was digested with HinfI to obtain a DNA fragment of about 0.95 kb. The termini of the fragment were changed flush with a Klenow fragment, and NheI linkers were linked thereto, followed by digestion with NheI. The resulting fragment was further digested with EcoRI to isolate an EcoRI-NheI fragment of about 0.9 kb coding for truncated gD.

Plasmid pJYL2299 containing *E. coli* heat-labile toxin gene [T. Yamamoto et al., *J. Bacteriol.*, 148, 983 (1981)] was digested with restriction enzyme HindIII to obtain a fragment of 0.77 kb containing B subunit. The resulting fragment was reacted with a digest of pBR322 with HindIII to obtain subcloning plasmid pBRLThB. The obtained plasmid was digested with restriction enzyme SacI, followed by reaction with T4 DNA polymerase and addition of NheI linker (pCGCTAGCG) (Pharmacia) using T4 DNA ligase to obtain plasmid pBRLThB-N. The plasmid was digested with restriction enzymes DraI and HindIII to obtain a DNA fragment of about 0.59 kb. To the fragment was added BglII linker (pGAAGATCTTC) (NEB) using T4 DNA ligase, followed by digestion with NheI and BglII to obtain a NheI-BglII fragment of 0.32 kb containing LThB-coding region.

The above described 0.9 kb- and 0.32 kb- DNA fragments and an about 3.9 kb fragment obtained by EcoRI-BglII digestion of pTB399 [Japanese Patent Unexamined Publication No. 61-63282/1986; R. Sasada et al., *Cell Structure and Function*, 12, 205 (1987)] were reacted with each other to obtain expression plasmid pHDT201.

Then, in order to express the fused gene in CHO cells and to enable gene amplification, a fragment of about 2.8 kb comprising a gD-LThB fused protein gene which was obtained by digesting pHDT201 with SalI and HindIII was reacted with a fragment of about 4.5 kb which was obtained by digesting dihydrofolate reductase (DHFR) gene expression plasmid pTB348 (Refer to Japanese Patent Unexamined Publication 63282/1986) with SalI and HindIII to obtain plasmid pHDTdhfr2 (FIG. 10).

EXAMPLE 6

Expression of Fused Protein Composed of HSV-1 truncated gD and LThB in Animal Cell The plasmid pHDTdhfr2 constructed in Example 5 was introduced into CHO cell DHFR⁻ strain by the calcium phosphate method similar to Example 2, to obtain a transformant which was converted to DHFR+.

The resulting transformant CHO-HDT-2-35 (IFO 50209, FERM BP-2590) was cultivated by a similar method to Example 2, and then was isotope-labeled with $^{35}$S-methionine, followed by immunoprecipitation of the gene product using a rabbit anti HSV-1 antibody and a goat anti choleratoxin antibody (LIST BIOLOGICAL LABORATORIES).

As a result, it was revealed that products of about 45 to 60 kdaltons which were reactive to both anti-HSV-1 and anti-choleratoxin antibodies were produced.

EXAMPLE 7

Construction of Gene Expression Plasmid for Fused Protein Composed of HSV-1 Truncated gD and LThB in Myeloma Cell The plasmid pHDT201 constructed in Example 5 was digested with restriction enzyme SalI and EcoRI to obtain a fragment of about 3.9 kb containing a fused gene composed of truncated gD and LThB. On the other hand, the truncated gD expression plasmid pHSDneol (Japanese Patent Application No. 2-177258/1990) having the neomycin-resistant gene was digested with SalI and EcoRI to obtain a fragment of about 4.4 kb containing the neomycin-resistant gene. These two fragments were reacted with each other to obtain expression plasmid pHDTneoI of the truncated gD-LThB fused gene having the neomycin-resistant gene (refer to FIG. 11).

EXAMPLE 8

Gene Expression of Fused Protein Composed of HSV-1 Truncated gD and LThB in Myeloma Cell Using the plasmid pHDTneoI constructed in Example 7, mouse myeloma cell Sp2/0-Ag14 (Dainippon Pharmaceutical) was transformed by electroporation using a Gene Pulser (Bio-Rad), followed by cultivation in RPMI1640 medium (Gibco) containing 200 μg/ml of G418 (Gibco) and 10% fetal calf serum to obtain G418-resistant transformants. A culture supernatant of the transformants was screened according to an enzyme immunoassay by a sandwich method using a microplate (Nunc) coated with rabbit anti-HSV-1 serum (Dakopatt) and biotinyl ani-HSV-1 & -2 antibody (Chemicon) to obtain clones in which truncated gD was expressed.

Of the clones, Sp-neo-HDT-13-71 relatively high in expression amount was cultivated in serum-free medium ASF104 (Ajinomoto), and 1 ml of a supernatant thereof was concentrated by Molcut (Millipore). Then, Laemmli buffer was added thereto to 50 μl, followed by heating at 100° C. for 5 minutes. After cooling, SDS-polyacrylamide gel electrophoresis was conducted, and further the western blotting was carried out using rabbit anti-HSV-1 serum (Dakopatt) and goat anti-cholera toxin serum. As a result, a band recognized by both of the antibodies was specifically detected.

EXAMPLE 9

Purification of Fused Protein Composed of Truncated gD and LThB (t-gD-LThB)

Transformant Sp-neo-HDT-13-71 obtained in Example 8 was suspended in serum-free medium ASF104 (Ajinomoto) and cultivated at 37° C. for 4 to 7 days in the presence of 5% $CO_2$. The culture was centrifuged at 4,000 rpm for 20 minutes with Hitachi CR26H centrifuge (Type 30 rotor) to give a culture supernatant (5.5 l). The supernatant was dialyzed against 20 mM phosphate buffer (pH 5.8) and filtered with No. 2 filter paper (Advantech Toyo). The filtrate was poured into a column (bed volume: 540 ml; $\phi 4.1 \times 41$ cm) charged with Sp-Toyopearl 650M (Toso) equilibrated with 20 mM phosphate buffer (pH 5.8). The column was washed with 20 mM phosphate buffer (pH 5.8), and then t-gD-LThB was eluted with a gradient of 0 to 1M NaCl (total 4 l). The t-gD-LThB fractions eluted by about 0.2 to 0.35M NaCl were concentrated to a volume of 8.3 ml by ultrafiltration (Amicon, YM10), and the concentrate was subjected to a column (bed volume: 198 ml; $\phi 1.6 \times 98.5$ cm) charged with Sephacryl S-300HR (Pharmacia) equilibrated with phosphate-buffered saline (PBS). The t-gD-LThB fractions were concentrated by ultrafiltration (Amicon, YM10) to obtain a purified sample (1.725 mg/0.845 ml).

EXAMPLE 11

Immunogenicity of Fused Protein Composed of HSV-1 Truncated gD and LThB (t-gD-LThB)

t-gD-LThB obtained in Example 10 was administered in an amount of 16 µl/mouse to the internal nares of BALB/c mice (female, 8 weeks old, Charles River). After 5 weeks, blood was collected and serum sample was prepared. The internal nares were washed with PBS several times to give a washing. The anti-HSV antibodies in these samples were determined by the following method.

An inactivated HSV-coated microplate of a human anti-HSV antibody determination kit (Herpes Stat, Whittaker Bioproducts, Lot No. 002706) was blocked with PBS containing 20% FCS at room temperature for 2 hours, followed by washing 3 times with PBS containing 0.05% Tween 20 (PBS-Tween). To this plate was added 100 µl/well of the serum sample diluted with 20% FCS/40 mM Tris-HCl (pH 7.5)/5% NaCl/0.05% Tween 20, followed by incubation at room temperature for 1 hour. The plate was washed 6 times with PBS-Tween, and then 100 µl of a 100- to 1,000-fold dilution of a peroxidase-labeled anti-mouse IgG antibody or anti-mouse IgA antibody (Zymed Laboratories) was added to each well, followed by incubation at room temperature for 30 minutes. The plate was washed 6 times with PBS-Tween, and then 100 µl of a substrate solution [2 mg/ml o-phenylenediamine/0.02% $H_2O_2$/0.1M citrate buffer (pH 4.5)] was added to each well, followed by reaction for 10 minutes. After 200 µl of 2N sulfuric acid was added to each well to terminate color development, absorbance was measured at 492 nm.

As a result, it was proved that IgG and IgA antibodies against HSV could effectively be induced in blood and/or internal nares by the administration of t-gD-LThB to internal nares.

The following references, which are referred to for their disclosures at various points in this application, are incorporated herein by reference.

Japanese Patent Application No. 63-180114/1988
Japanese Patent Application No. 1-158238/1989
Japanese Patent Application No. 1-308941/1989
Virology, 133, 301 (1984)
J. Virol., 53, 243 (1985)
J. Bacteriol., 143, 652 (1980)
Mol. Cell. Biol., 4. 771 (1984)
Current Genetics, 10, 443(1986)
Proc. Natl. Acad. Sci. U.S.A., 75, 1929 (1978)
Virology, 52, 456 (1973)
Proc. Natl. Acad. Sci. U.S.A., 77, 4505 (1980)
Science, 122, 501 (1952)
Virology, 8, 396 (1959)
The Journal of the American Medical Association, 199, 519 (1967)
Proceeding of the Society for the Biological Medicine, 73, 1 (1950)
Japanese Patent Unexamined Publication No. 61-63282/1986
Cell Structure and Function, 12, 205 (1987)
Proc. Natl. Acad. Sci. U.S.A., 77, 4216–4220 (1980)
Science, 221, 551–553 (1983)
Nature, 227, 680 (1970)
J. Bacteriol., 148, 983 (1981)
Japanese Patent Application No. 2-177258/1990

What is claimed is:

1. A fused protein comprising (a) a glycoprotein gD lacking a transmembrane domain of herpes simplex virus type I and (b) a heat-labile enterotoxin B subunit, wherein the glyprotein gD is at the amino terminal side and the heat-labile enterotoxin B subunit is at the carboxyl terminal side.

2. A fused protein in accordance with claim 1, wherein the heat-labile enterotoxin B subunit is a product of enterotoxigenic Escherichia coli derived from a human.

3. A method for targetting nasal mucosa tissues with a heat-labile enterotoxn B subunit which comprises administering a therapeutically effective amount of the fused protein of claim 1.

* * * * *